(12) United States Patent
Fairbrother et al.

(10) Patent No.: US 7,067,274 B2
(45) Date of Patent: Jun. 27, 2006

(54) COMPOSITIONS AND METHODS FOR THE SCREENING PRO-APOPTOTIC COMPOUNDS

(75) Inventors: Wayne J. Fairbrother, Burlingame, CA (US); Matthew C. Franklin, San Francisco, CA (US); Heidi Jenii Ackerly Wallweber, La Honda, CA (US); Linda Orren Elliott, Half Moon Bay, CA (US); Saloumeh Kadkhodayan, Castro Valley, CA (US); Domagoj Vucic, San Francisco, CA (US); Guy Salvesen, Encinitas, CA (US)

(73) Assignees: Genentech, Inc., South San Francisco, CA (US); The Burnham Institute, Encinitas, CA (US)

( * ) Notice: Subject to any disclaimer, the term of this patent is extended or adjusted under 35 U.S.C. 154(b) by 76 days.

(21) Appl. No.: 10/983,495

(22) Filed: Nov. 8, 2004

(65) Prior Publication Data

US 2005/0214802 A1 Sep. 29, 2005

Related U.S. Application Data

(60) Provisional application No. 60/519,863, filed on Nov. 13, 2003.

(51) Int. Cl.
*C12Q 1/00* (2006.01)
*C12Q 1/37* (2006.01)
*G01N 33/53* (2006.01)
(52) U.S. Cl. .............................. 435/23; 435/7.1; 435/6
(58) Field of Classification Search ............. 435/4–7.1, 435/23
See application file for complete search history.

(56) References Cited

FOREIGN PATENT DOCUMENTS

| WO | WO 00/00823 | 6/2000 |
|---|---|---|
| WO | WO 00/39585 | 6/2000 |
| WO | WO 2004/106371 A1 | 12/2004 |

OTHER PUBLICATIONS

Boatright et al., "A Unified Model for Apical Caspase Activation" *Molecular Cell* 11:529-541 (2003).
Chai et al., "Structural and Biochemical Basis of Apoptotic Activation by Smac/DIABLO" *Nature* 406:855-862 (Aug. 2000).
Chen et al., "grim, a novel cell death gene in *Drosophila*" *Genes & Development* 10:1773-1782 (1996).
Christich et al., "The Damage-Responsive *Drosophila* Gene sickle Encodes a Novel IAP Binding Protein Similar to but Distinct from reaper, grim, and hid" *Current Biology* 12:137-140 (2002).
Crook et al., "An Apoptosis-Inhibiting Baculovirus Gene with a Zinc Finger-Like Motif" *Journal of Virology* 67(4):2168-2174 (Apr. 1993).
Derossi et al., "Trojan Peptides: The Penetratin System for Intracellular Delivery" *Trends Cell Biol.* 8:84-87 (Feb. 1998).
Deveraux et al., "Endogenous Inhibitors of Caspases" *J. Clin. Immunol.* 19(6):388-398 (1999).
Deveraux, Q. & Reed, J., "IAP family proteins-suppressors of apoptosis" *Genes Dev* 13:239-252 (1999).
Franklin et al., "Structure and Function Analysis of Peptide Antagonists of Melanoma Inhibitor of Apoptosis (ML-IAP)" *Biochemistry* 42:8223-8231 (2003).
Goyal et al., "Induction of apoptosis by *Drosophila* reaper, hid and grim through inhibition of IAP function" *Embo Journal* 19:589-597 (2000).
Grether et al., "The head involution defective gene of *Drosophila melanogaster* functions in programmed cell death" *Genes Dev* 9:1694-1708 (1995).
Hinds et al., "Solution Structure of a Baculoviral Inhibitor of Apoptosis (IAP) Repeat" *Nat. Struct. Biol.* 6:648-651 (Jul. 1999).
Jones et al., "Improved methods for building protein models in electron density maps and the location of errors in these models" *Acta Cryst.* A47:110-119 (1991).
Kolb et al., "Use of a Novel Homogeneous Fluorescent Technology in High Throughput Screening" *J. Biomol. Screening* 1(4):203-210 (1996).
Liu et al., "Eradication of Large Colon Tumor Xenografts by Targeted Delivery of Maytansinoids." *Proc. Natl. Acad. Sci. USA* 93:8618-8623 (Aug. 1996).

(Continued)

*Primary Examiner*—Maryam Monshipouri
*Assistant Examiner*—Suzanne M. Mayer
(74) *Attorney, Agent, or Firm*—David A. Carpenter

(57) ABSTRACT

The present invention is directed to compositions of matter useful for the enhancement of apoptosis in mammals and to methods of using those compositions of matter for the same.

4 Claims, 14 Drawing Sheets

OTHER PUBLICATIONS

Liu et al., "Structural Basis for Binding of Smac/DIABLO to the XIAP BIR3 Domain" *Nature* 408:1004-1008 (Dec. 2000).

Murshudov et al., "Refinement of Macromolecular Structures by the Maximum-Likelihood Method" *Acta Cryst.* D53:240-255 (1997).

Perrakis et al, "ARP/wARP and molecular replacement" *Acta Crystallographica* D57:1445-1450 (2001).

Prochiantz, A., "Getting Hydrophilic Compounds into Cells: Lessons from Homeopeptides" *Curr. Opinion Neurobiol.* 6(5):629-634 (1996).

Salvesen and Nagese, "Determination of protease mechanism" *Proteolytic enzymes: A practical approach*, R.J. Beynon and J.S. Bond, Oxford, IRL Press pp. 83-104 (1989).

Shiozaki et al., "Mechanism of XIAP-Mediated Inhibition of Caspase-9" *Molecular Cell* 11:519-527 (2003).

Shuker et al., "Discovering High-Affinity Ligands for Proteins: SAR by NMR" *Science* 274:1531-1534 (Nov. 1996).

Srinivasula et al., "A conserved XIAP-interaction motif in caspase-9 and Smac/DIABLO regulates caspase activity and apoptosis" *Nature* 410:112-116 (2001).

Srinivasula et al., "sickle, a Novel *Drosophila* Death Gene in the reaper/hid/grim Region, Encodes an IAP-Inhibitory Protein" *Current Biology* 12:125-130 (2002).

Sun et al., "NMR Structure and Mutagenesis of the Inhibitor-of-Apoptosis Protein XIAP" *Nature* 401:818-822 (Oct. 1999).

Sun et al., "NMR Structure and Mutagenesis of the Third Bir Domain of the Inhibitor of Apoptosis Protein XIAP" *Journal of Biological Chemistry* 275:33777-33781 (Oct. 2000).

Takahashi et al., "A Single BIR Domain of XIAP Sufficient for Inhibiting Caspases" *The Journal of Biological Chemistry* 273:7787-7790 (1998).

Tenev et al., "Jafrac2 is an IAP antagonist that promotes cell death by liberating Dronc from DIAP1" *Embo Journal* 21:5118-5129 (2002).

Thompson, "Apoptosis in the Pathogenesis and Treatment of Disease" *Science* 267:1456-1462 (1995).

Vucic et al., "ML-IAP, A Novel Inhibitor of Apoptosis that is Preferentially Expressed in Human Melanomas" *Current Bio.* 10:1359-1366 (Oct. 2000).

Vucic et al., "SMAC Negatively Regulates the Anti-apoptotic Activity of Melanoma Inhibitor of Apoptosis (ML-IAP)" *The Journal of Biological Chemistry* 277:12275-12279 (2002).

White et al., "Genetic Control of Programmed Cell Death in *Drosophila*" *Science* 264:677-683 (1994).

Wing et al., "*Drosophila* sickle Is a Novel grim-reaper Cell Death Activator" *Current Biology* 12:131-135 (2002).

Wu et al., "Structural Analysis of a Functional DIAP1 Fragment Bound to Grim and Hid Peptides" *Mol. Cell.* 8:95-104 (Jul. 2001).

Wu et al., "Structural Basis of IAP Recognition by Smac/DIABLO" *Nature* 408:1008-1012 (Dec. 2000).

Sanna M et al., "IAP suppression of apoptosis involves distinct mechanisms: the TAK1/JNK1 signaling cascade and caspase inhibition" *Mol Cell Biol.* 22(6):1754-1766 (Mar. 2002).

Vucic D et al., "Engineering ML-IAP to produce an extraordinarily potent caspase 9 inhibitor: implications for Smac-dependent anti-apoptotic activity of ML-IAP" *Biochemical Journal* 385(Part 1):11-20 (Jan. 2005).

FIGURE 1

ATGGGCAGCAGCCATCATCATCATCATCACAGCAGCGGCCTGGTGCCGCGCGGCAGCCATATGCTCGAG
ACAGAGGAGGAAGAGGAGGAGGGCGCCGGGGCCACCTTGTCCAGGGGGCCTGCCTTCCCCGGCATGGGC
TCTGAGGAGTTGCGTCTGGCCTCCTTCTATGACTGGCCGCTGACTGCTGAGGTGCCACCCGAGCTGCTG
GCTGCTGCCGGCTTCTTCCACACAGGCCATCAGGACAAGGTGAGGTGCTTCTTCTGCTATGGGGCCTG
CAGAGCTGGAAGCGCGGGGACGACCCCTGGACGGAGCATGCCAAGTGGTTCCCCGGTTGTCAGTTCCTG
CTCCGGTCAAAAGGACAAGAATATATAAACAATATTCATTTAACTCATTCACTT

FIGURE 2

MGSSHHHHHHSSGLVPRGSHMLETEEEEEEGAGATLSRGPAFPGMGSEELRLASFYDWPLTAEVPPELL
AAAGFFHTGHQDKVRCFFCYGGLQSWKRGDDPWTEHAKWFP<u>G</u>CQFLLRSKG<u>QEYINN</u>IHLTHS<u>L</u>

FIGURE 3

| | | |
|---|---|---|
| MLBIR | 63 | T E E E E E E G A G A T L S R G P A F P G M G S E E L R L A S F Y D W P L T A | 101 |
| MLBIR-Q | 63 | T E E E E E E G A G A T L S R G P A F P G M G S E E L R L A S F Y D W P L T A | 101 |
| MLXBIR3(SG) | 63 | T E E E E E E G A G A T L S R G P A F P G M G S E E L R L A S F Y D W P L T A | 101 |
| XIAP-BIR3 | 241 | S D A V S S D R N F P N S T N L P R N P S M A D Y E A R I F T F G T W I Y S V | 279 |
| MLBIR | 102 | E V P P E L L A A A G F F H T G H Q D K V R C F F C Y G G L Q S W K R G D D P | 140 |
| MLBIR-Q | 102 | E V P P E L L A A A G F F H T G H Q D K V R C F F C Y G G L Q S W K R G D D P | 140 |
| MLXBIR3(SG) | 102 | E V P P E L L A A A G F F H T G H Q D K V R C F F C Y G G L Q S W K R G D D P | 140 |
| XIAP-BIR3 | 280 | N K - E Q L A R A G F Y A L G E G D K V K C F H C G G G L T D W K P S E D P | 316 |
| MLBIR | 141 | W T E H A K W F P S C Q F L L R S K G R D F V H S V Q E T H S Q L L G S W D P | 179 |
| MLBIR-Q | 141 | W T E H A K W F P S C Q F L L R S K G R D F V H S V Q E T H S Q | 172 |
| MLXBIR3(SG) | 141 | W T E H A K W F P G C Q F L L R S K G Q E Y I N N I H L T H S L | 172 |
| XIAP-BIR3 | 317 | W E Q H A K W Y P G C K Y L L E Q K G Q E Y I N N I H L T H S L | 348 |

FIGURE 14

MGSSHHHHHHSSGLVPRGSHMLETEEEEEEGEGETLSRGPAEPGMGSEEDRLASFYDWPL
TAEVPPELLAAAGFFHTGHQDKVRCFFCYGGLQSWKRGDDPWTEHAKWFPGCQFLLRSKG
QEYINNIHLTHSL

COMPOSITIONS AND METHODS FOR THE SCREENING PRO-APOPTOTIC COMPOUNDS

PRIORTY

This application claims priority to U.S. Provisional Application No.: 60/519,863 filed Nov. 13, 2003, to which U.S. Provisional Applications claim priority under 35 U.S.C. §119, the entire disclosure of which is hereby incorporated by reference in its entirety.

FIELD OF THE INVENTION

The present invention is directed to compositions of matter useful for screening for compositions of matter which enhance apoptosis in mammals, and to methods of screening.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456–1462).

Some of the key effector molecules in apoptosis are the caspases (cysteine containing aspartate specific proteases). Caspases are strong proteases, cleaving after aspartic acid residues and once activated, digest vital cell proteins from within the cell. Since caspases are such highly active proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism of regulation is through a family of proteins that bind and inhibit caspases.

A family of molecules that inhibit caspases are the Inhibitors of Apoptosis (IAP) (Deveraux et al., J Clin Immunol (1999), 19:388–398). IAPs were originally discovered in baculovirus by their functional ability to substitute for P35 protein, an anti-apoptotic gene (Crook et al. (1993) J Virology 67, 2168–2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 80 residues comprising 5 alpha-helices and 3 beta strands, with cysteine and histidine residues that coordinate the zinc ion (Hinds et al., (1999) Nat. Struct. Biol. 6, 648–651.; Sun et al., (1999) Nature 401, 818–22.; Sun et al., (2000) J. Biol Chem. 275,33777–81).

All IAP proteins contain one to three copies of the baculoviral IAP repeat (BIR), a zinc-binding domain of ~80 amino acids, that are necessary for their interactions with a number of cytosolic target proteins, including activated caspases-3, -7, and -9, and natural IAP protein antagonists such as mature Smac/DIABLO and HtrA2/Omi. Different BIR domains, however, have differing affinities for these proteins, and thus distinct functions in the regulation of apoptosis. For instance, the second BIR domain of X-chromosome-linked IAP (XIAP) together with the immediately preceding linker region (XIAP-BIR2) binds to and inhibits caspases-3 and -7 with inhibition constants in the range of 2–10 nM (Takahashi et al., (1998) J Biol Chem 273(14): 7787–90.; Sun et al., (1999) Nature 401 (6755): 818–22), while the third BIR domain of XIAP (XIAP-BIR3) specifically inhibits caspase-9 with an inhibition constant in the range of 10–20 nM (Deveraux et al., (1999) Genes Dev 13: 239–252; Liu et al., (2000) Nature 408(6815): 1004–8.; Sun et al., (2000) J Biol Chem 275(43): 33777–81). By contrast, the single BIR domain of melanoma inhibitor of apoptosis (ML-IAP) has been shown to inhibit weakly caspases-3 and -9, but not caspase-7, although inhibition constants have not been reported (Vucic et al., (2000) Curr Biol 10(21): 1359–66).

Melanoma IAP (ML-IAP) is an IAP whose expression is strongly upregulated in melanoma (Vucic et al., (2000) Current Bio 10:1359–1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as Adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is through inhibition of caspase 3 and 9. ML-IAP did not effectively inhibit caspases 1, 2, 6, 7 or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins Smac/DIABLO act to block the IAPs and allow apoptosis to proceed. It was shown that during normal apoptosis, Smac is processed into an active form and is released from the mitochondria into the cytoplasm where it physically binds to IAPs and prevents the IAP from binding to a caspase. This inhibition of the IAP allows the caspase to remain active and thus proceed with apoptosis.

The proapoptotic function of these IAP protein antagonists is dependent on a conserved four-residue IAP protein-interaction motif (A-V/I-P/A-I/F/Y) found at the N-termini of the mature proteins Chai et al., (2000) Nature 406: 855–862; Srinivasula et al., (2001) Nature 410(6824): 112–6). This conserved motif is also found at the N-termini of the Drosophila proteins Reaper, Hid, Grim, Sickle, and Jafrac2, that also antagonize IAP proteins and are thus functional homologues of Smac/DIABLO (White et al., (1994) Science 264(5159): 677–83.; Grether et al., (1995) Genes Dev 9(14): 1694–708; Chen et al., (1996) Genes Dev 10(14): 1773–82; Goyal et al., (2000) Embo J 19(4): 589–97; Christich et al., (2002) Curr Biol 12(2): 137–40; Srinivasula et al., (2002) Curr Biol 12(2): 125–30; Tenev et al., (2002) Embo J 21(19): 5118–29.; Wing et al., (2002) Curr Biol 12(2): 131–5.). Structural studies have shown that these N-terminal peptides bind to a surface groove on the BIR domains, with the binding being stabilized by electrostatic interactions involving the conserved N-terminal alanine residue of the peptide, together with several intermolecular hydrogen bonds and hydrophobic interactions (Liu et al., (2000) Nature 408:1004–1008, Wu et al., (2000) Nature 408 1008–1012; Wu et al., (2001) Mol. Cell 8, 95–104; Srinivasula et al., (2002) Curr. Biol. 12, 125–30; Franklin et al., (2003) Biochem. 42 8223–31).

Despite the above identified advances in apoptosis research, there is a great need for additional diagnostic and therapeutic agents capable of enhancing apoptosis in a mammal with the goal of inhibiting the progression of cancer. The present invention relates to a chimeric ML-IAP polypeptide in which certain residues correspond to those found in XIAP-BIR3, while the remainder corresponds to ML-IAP. The chimeric protein is shown to bind and inhibit caspase-9 significantly better than either of the native ML-IAP or XIAP, but binds Smac-based peptides and mature Smac with affinities similar to those of native ML-IAP. The improved caspase-9 inhibition of the chimeric ML-IAP polypeptide is correlated with increased inhibition of doxorubicin-induced apoptosis when transfected into MCF7 cells. Accordingly, the present invention relates to use of the ML-IAP chimeric polypeptide and methods for screening for IAP antagonists.

SUMMARY OF THE INVENTION

In one embodiment, the invention provides an ML-IAP chimera. Such chimeras can be used for screening methods for identifying agents that alter the association of the ML-IAP chimera and a caspase. Preferably, the caspase is caspase-3 or caspase-9.

In another embodiment, the invention provides for methods of altering the apoptotic profile of a population of cells by transfecting the cells with an ML-IAP chimera and then contacting the cells with an IAP inhibitor and determining if the cells are more susceptible to apoptosis. In a preferred embodiment, the transfected cells are also treated with a secondary apoptotic agent, such as APO2L.

Yet another embodiment of the present invention is directed to a method of determining the presence of a ML-IAP chimera inhibitor in a sample suspected of containing the IAP inhibitor, wherein the method comprises exposing the sample to a ML-IAP chimera that binds to the IAP inhibitor and determining binding of the ML-IAP chimera to the IAP inhibitor in the sample, wherein the presence of such binding is indicative of the presence of the IAP inhibitor in the sample. Optionally, the sample may contain cells suspected of expressing the IAP inhibitor. The ML-IAP chimera polypeptide employed in the method may optionally be detectably labeled, attached to a solid support, or the like.

Yet another embodiment of the present invention is directed to a method of binding an IAP inhibitor to a cell that expresses a ML-IAP chimera, wherein the method comprises contacting a cell that expresses a ML-IAP chimera with said IAP inhibitor under conditions which are suitable for binding of the ML-IAP chimera to said IAP inhibitor and allowing binding there between.

Yet another embodiment of the present invention is directed to a method of identifying IAP inhibitors by use of the crystal structure of a ML-IAP chimera, wherein said crystal structure is used to identify contact residues between the BIR domain and a potential IAP inhibitor. Such contact residues and neighboring residues are candidates for substitution according to the techniques elaborated herein. Once such variants are generated, the panel of variants is subjected to screening as described herein and IAP inhibitors with superior properties in one or more relevant assays will be indentified.

In another embodiment, the invention provides an antibody which specifically binds to any of the above or below described polypeptides. Optionally, the antibody is a monoclonal antibody, humanized antibody, antibody fragment or single-chain antibody. In one aspect, the present invention concerns an isolated antibody which binds an ML-IAP chimera polypeptide. In another aspect, the antibody inhibits or neutralizes the activity of a ML-IAP chimera (an antagonist antibody). In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a monoclonal antibody, a single-chain antibody, or an anti-idiotypic antibody.

In yet another embodiment, the present invention provides a composition comprising an anti-ML-IAP chimera antibody in admixture with a pharmaceutically acceptable carrier. In one aspect, the composition comprises a therapeutically effective amount of the antibody. Preferably, the composition is sterile. The composition may be administered in the form of a liquid pharmaceutical formulation, which may be preserved to achieve extended storage stability. Alternatively, the antibody is a monoclonal antibody, an antibody fragment, a humanized antibody, or a single-chain antibody.

In a further embodiment, the invention concerns an article of manufacture, comprising:

(a) a composition of matter comprising a ML-IAP chimera polypeptide or agonist or antagonist thereof;

(b) a container containing said composition; and a label affixed to said container, or a package insert included in said container referring to the use of said ML-IAP chimera polypeptide or agonist or antagonist thereof in the alleviation of cancer.

The composition may comprise a therapeutically effective amount of the ML-IAP chimera polypeptide or the agonist or antagonist thereof.

In yet another embodiment, the present invention concerns a method of diagnosing cancer in a mammal, comprising detecting the level of expression of a gene encoding a IAP inhibitor (a) in a test sample of tissue cells obtained from the mammal, and (b) in a control sample of known normal tissue cells of the same cell type, wherein a higher or lower expression level in the test sample as compared to the control sample indicates the presence of cancer in the mammal from which the test tissue cells were obtained.

In another embodiment, the present invention concerns a method of diagnosing cancer in a mammal, comprising (a) contacting an anti-ML-IAP chimera antibody with a test sample of tissue cells obtained from the mammal, and (b) detecting the formation of a complex between the antibody and a ML-IAP chimera polypeptide, in the test sample; wherein the formation of said complex is indicative of the presence or absence of said cancer. The detection may be qualitative or quantitative, and may be performed in comparison with monitoring the complex formation in a control sample of known normal tissue cells of the same cell type. A larger quantity of complexes formed in the test sample indicates the presence or absence of a cancer in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of suffering from cancer.

In another embodiment, the invention provides a method for determining the presence of a IAP polypeptide in a sample comprising exposing a test sample of cells suspected of containing the IAP polypeptide to an anti-ML-IAP chimera antibody and determining the binding of said antibody to said cell sample. In a specific aspect, the sample comprises a cell suspected of containing the IAP polypeptide and the antibody binds to the cell. The antibody is preferably detectably labeled and/or, bound to a solid support.

In another embodiment, the present invention concerns an cancer-related disease diagnostic kit, comprising an anti-ML-IAP chimera antibody and a carrier in suitable packaging. The kit preferably contains instructions for using the antibody to detect the presence of the IAP polypeptide. Preferably the carrier is pharmaceutically acceptable.

In another embodiment, the present invention concerns a diagnostic kit, containing an anti-ML-IAP chimera antibody in suitable packaging. The kit preferably contains instructions for using the antibody to detect the ML-IAP chimera.

In another embodiment, the present invention concerns a method for identifying an agonist of a ML-IAP chimera polypeptide comprising:

(a) contacting cells and a test compound to be screened under conditions suitable for the induction of a cellular response normally induced by a IAP polypeptide; and (b) determining the induction of said cellular response to determine if the test compound is an effective agonist, wherein the induction of said cellular response is indicative of said test compound being an effective agonist.

In another embodiment, the invention concerns a method for identifying a compound capable of inhibiting the activity of a ML-IAP chimera polypeptide comprising contacting a candidate compound with a ML-IAP chimera polypeptide under conditions and for a time sufficient to allow these two components to interact and determining whether the activity of the ML-IAP chimera polypeptide is inhibited. In a specific aspect, either the candidate compound or the ML-IAP chimera polypeptide is immobilized on a solid support. In another aspect, the non-immobilized component carries a detectable label. In a preferred aspect, this method comprises the steps of:

(a) contacting cells and a test compound to be screened in the presence of a ML-IAP chimera polypeptide under conditions suitable for the induction of a cellular response normally induced by a IAP polypeptide; and (b) determining the induction of said cellular response to determine if the test compound is an effective antagonist.

In another embodiment, the invention provides a method for identifying a compound that inhibits the expression of a ML-IAP chimera polypeptide in cells that normally express the polypeptide, wherein the method comprises contacting the cells with a test compound and determining whether the expression of the ML-IAP chimera polypeptide is inhibited. In a preferred aspect, this method comprises the steps of:

(a) contacting cells and a test compound to be screened under conditions suitable for allowing expression of the ML-IAP chimera polypeptide; and (b) determining the inhibition of expression of said polypeptide.

In yet another embodiment, the present invention concerns a method for treating cancer in a mammal that suffers therefrom comprising administering to the mammal a nucleic acid molecule that codes for either (a) a ML-IAP chimera polypeptide, (b) an agonist of a ML-IAP chimera polypeptide or (c) an antagonist of a ML-IAP chimera polypeptide, wherein said agonist or antagonist may be an anti-ML-IAP chimera antibody. In a preferred embodiment, the mammal is human. In another preferred embodiment, the nucleic acid is administered via ex vivo gene therapy. In a further preferred embodiment, the nucleic acid is comprised within a vector, more preferably an adenoviral, adeno-associated viral, lentiviral or retroviral vector.

In yet another aspect, the invention provides a recombinant viral particle comprising a viral vector consisting essentially of a promoter, nucleic acid encoding (a) a ML-IAP chimera polypeptide, (b) an agonist polypeptide of a ML-IAP chimera polypeptide, or (c) an antagonist polypeptide of a ML-IAP chimera polypeptide, and a signal sequence for cellular secretion of the polypeptide, wherein the viral vector is in association with viral structural proteins. Preferably, the signal sequence is from a mammal.

In a still further embodiment, the invention concerns an ex vivo producer cell comprising a nucleic acid construct that expresses retroviral structural proteins and also comprises a retroviral vector consisting essentially of a promoter, nucleic acid encoding (a) ML-IAP chimera polypeptide, (b) an agonist of a ML-IAP chimera polypeptide or (c) an antagonist of a ML-IAP chimera polypeptide, and a signal sequence for cellular secretion of the polypeptide, wherein said producer cell packages the retroviral vector in association with the structural proteins to produce recombinant retroviral particles.

In a still further embodiment, the invention provides a method of increasing the proliferation of cells in a mammal comprising administering to said mammal (a) a ML-IAP chimera polypeptide, (b) or an agonist of a ML-IAP chimera polypeptide, wherein the proliferation of cells in the mammal is increased.

In a still further embodiment, the invention provides a method of decreasing the proliferation of cells in a mammal comprising administering to said mammal (a) a ML-IAP chimera polypeptide, or (b) an antagonist of a ML-IAP chimera polypeptide, wherein the proliferation of cells in the mammal is decreased.

In a still further embodiment, the invention provides a method of decreasing the apoptosis of cells in a mammal comprising administering to said mammal (a) a ML-IAP chimera polypeptide, (b) or an agonist of a ML-IAP chimera polypeptide, wherein the apoptosis of cells in the mammal is decreased.

In a still further embodiment, the invention provides a method of increasing the apoptosis of cells in a mammal comprising administering to said mammal an antagonist of a ML-IAP chimera polypeptide, wherein the apoptosis of cells in the mammal is increased.

ADDITIONAL EMBODIMENTS

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a ML-IAP chimera polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a ML-IAP chimera polypeptide having a the amino acid sequence as disclosed herein, or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a the ML-IAP chimera polypeptide cDNA as disclosed herein, or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs as disclosed herein, or (b) the complement of the DNA molecule of (a).

Another aspect the invention provides an isolated nucleic acid molecule comprising a nucleotide sequence encoding a ML-IAP chimera polypeptide or is complementary to such encoding nucleotide sequence.

Another embodiment is directed to fragments of a ML-IAP chimera polypeptide coding sequence, or the complement thereof, that may find use as, for example, hybridization probes, for encoding fragments of a ML-IAP chimera polypeptide that may optionally encode a polypeptide comprising a binding site for an anti-ML-IAP chimera antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 206 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a ML-IAP chimera polypeptide-encoding nucleotide sequence may be determined in a routine manner by aligning the ML-IAP chimera polypeptide-encoding nucleotide sequence with other known nucleotide sequences using any of a number of well known sequence alignment programs and determining which ML-IAP chimera polypeptide-encoding nucleotide sequence fragment(s) are novel. All of such ML-IAP chimera polypeptide-encoding nucleotide sequences are contemplated herein. Also contemplated are the ML-IAP chimera polypeptide fragments encoded by these nucleotide molecule fragments, preferably those ML-IAP chimera polypeptide fragments that comprise a binding site for an anti-ML-IAP chimera antibody.

In another embodiment, the invention provides isolated ML-IAP chimera polypeptide encoded by any of the isolated nucleic acid sequences herein above identified.

In a certain aspect, the invention concerns an isolated ML-IAP chimera polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a ML-IAP chimera polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated ML-IAP chimera polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alterna-tively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs as disclosed herein.

In a specific aspect, the invention provides an isolated ML-IAP chimera polypeptide without the N-terminal signal sequence and/or the initiating methionine and is encoded by a nucleotide sequence that encodes such an amino acid sequence as herein before described. Processes for producing the same are also herein described, wherein those processes comprise culturing a host cell comprising a vector which comprises the appropriate encoding nucleic acid molecule under conditions suitable for expression of the ML-IAP chimera polypeptide and recovering the ML-IAP chimera polypeptide from the cell culture.

Processes for producing the same are also herein described, wherein those processes comprise culturing a host cell comprising a vector which comprises the appropriate encoding nucleic acid molecule under conditions suitable for expression of the ML-IAP chimera polypeptide and recovering the ML-IAP chimera polypeptide from the cell culture.

In yet another embodiment, the invention concerns agonists and antagonists of a native ML-IAP chimera polypeptide as defined herein. In a particular embodiment, the agonist or antagonist is an anti-ML-IAP chimera antibody or a small molecule.

In a further embodiment, the invention concerns a method of identifying agonists or antagonists to a ML-IAP chimera polypeptide which comprise contacting the ML-IAP chimera polypeptide with a candidate molecule and monitoring a biological activity mediated by said ML-IAP chimera polypeptide. Preferably, the ML-IAP chimera polypeptide is a native ML-IAP chimera polypeptide.

In a still further embodiment, the invention concerns a composition of matter comprising a ML-IAP chimera polypeptide, or an agonist or antagonist of a ML-IAP chimera polypeptide as herein described, or an anti-ML-IAP chimera antibody, in combination with a carrier. Optionally, the carrier is a pharmaceutically acceptable carrier.

Another embodiment of the present invention is directed to the use of a ML-IAP chimera polypeptide, or an agonist or antagonist thereof as herein before described, or an anti-ML-IAP chimera antibody, for the preparation of a medicament useful in the treatment of a condition which is responsive to the ML-IAP chimera polypeptide, an agonist or antagonist thereof or an anti-ML-IAP chimera antibody.

BRIEF DESCRIPTION OF THE DRAWINGS

FIG. 1. Nucleic acid sequence of the ML-IAP chimera (MLXBIR3SG).

FIG. 2. Amino acid sequence of the ML-IAP chimera (MLXBIR3SG). The XIAP BIR domain is underlined, as is the mutation of serine 150 to a glycine.

FIG. 3. Amino acid aligment of ML-BIR (Wild type), ML-BIRQ (C-terminal truncated wild type), MLXBIR3SG (ML-LIAP chimera. ML-IAP framework with the XIAP BIR3 domain inserted, and a S150G change), XAP (Wild type).

FIG. 14. Shows the sequence of the ML-IAP chimera (SEQ ID NO:6) which produces an improved NMR spectra.

DETAILED DESCRIPTION OF THE PREFERRED EMBODIMENTS

Definitions

Figure 4:
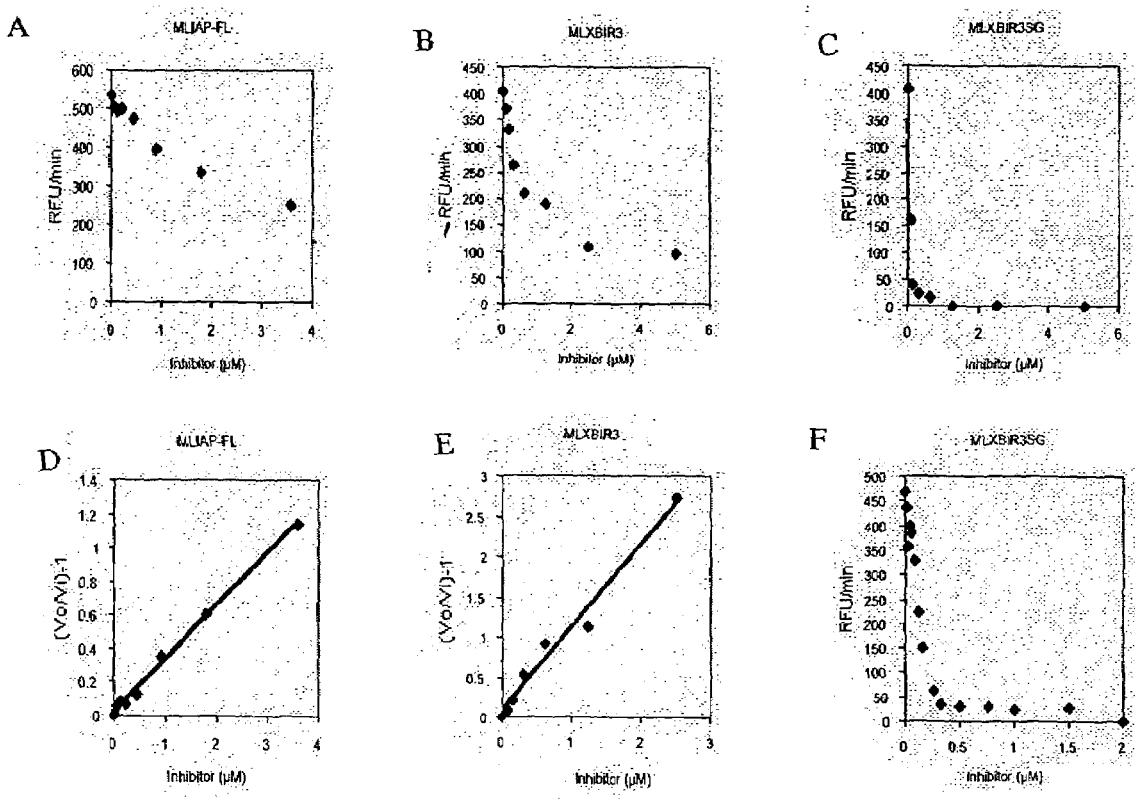
FIG. 4A–F Inhibition of caspase-9 by full-length ML-IAP (MLIAP-FL), and the chimeric constructs MLXBIR3 and MLXBIR3SG. For each inhibitor protein the caspase-9 hydrolysis rate ($v_i$; RFU/min) is plotted versus inhibitor concentration (FIG. 4A–4C). Plots of $(v_0/v_i)$-1 versus inhibitor concentration, from which $K_i$(app) is extracted, are also shown for MLIAP-FL and MLXBIR3 (FIG. 4D–4F).

"ML-IAP chimera polypeptide variant" means an active ML-IAP chimera polypeptide as defined above or below having at least about 80% amino acid sequence identity with a ML-IAP chimera polypeptide sequence as disclosed herein, a ML-IAP chimera polypeptide sequence lacking a BIR domain as disclosed herein, or any other fragment of a ML-IAP chimera polypeptide sequence as disclosed herein. Such ML-IAP chimera polypeptide variants include, for instance, ML-IAP chimera polypeptides wherein one or more amino acid residues are added, or deleted, at the N- or C-terminus of the ML-IAP chimera amino acid sequence. Ordinarily, a ML-IAP chimera polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a ML-IAP chimera polypeptide sequence as disclosed herein, a ML-IAP chimera polypeptide sequence lacking a BIR domain as disclosed herein, or any other specifically defined fragment of a ML-IAP chimera polypeptide sequence as disclosed herein. Ordinarily, ML-IAP chimera variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the ML-IAP chimera polypeptide sequences identified herein is defined as the percentage of amino acid residues in a candidate sequence that are identical with the amino acid residues in the specific ML-IAP chimera polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "ML-IAP chimera", wherein "ML-IAP chimera" represents the amino acid sequence of a hypothetical ML-IAP chimera polypeptide of interest, "Comparison Protein" represents the amino acid sequence of a polypeptide against which the "ML-IAP chimera" polypeptide of interest is being compared, and "X", "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the polypeptide of interest having a sequence derived from the native polypeptide and the comparison amino acid sequence of interest (i.e., the sequence against which the polypeptide of interest is being compared which may be a variant polypeptide) as determined by WU-BLAST-2 by (b) the total number of amino acid residues of the polypeptide of interesl For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the polypeptide of interest.

Percent amino acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"ML-IAP chimera variant polynucleotide" or "ML-IAP chimera variant nucleic acid sequence" means a nucleic acid molecule which encodes a ML-IAP chimera polypeptide as defined below and which has at least about 80% nucleic acid sequence identity with a nucleotide acid sequence encoding a ML-IAP chimera polypeptide sequence as disclosed herein, or any other fragment of a ML-IAP chimera polypeptide sequence as disclosed herein. Ordinarily, a ML-IAP chimera variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a ML-IAP chimera polypeptide sequence as disclosed herein, or any other fragment of a MLIAP chimera polypeptide sequence as disclosed herein. Variants do not encompass the native nucleotide sequence.

Ordinarily, ML-IAP chimera variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to ML-IAP chimera-encoding nucleic acid sequences identified herein is defined as the percentage of nucleotides in a candidate sequence that are identical with the nucleotides in the nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "ML-IAP chimera-DNA", wherein "ML-IAP chimera-DNA" represents a hypothetical ML-IAP chimera-encoding nucleic acid sequence of interest, "Comparison DNA" represents the nucleotide sequence of a nucleic acid molecule against which the "ML-IAP chimera-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the polypeptide-encoding nucleic acid molecule of interest having a sequence derived from the native sequence polypeptide-encoding nucleic acid and the comparison nucleic acid molecule of interest (i.e., the sequence against which the polypeptide-encoding nucleic acid molecule of interest is being compared which may be a variant polynucleotide) as determined by WU-BLAST-2 by (b) the total number of nucleotides of the polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the ML-IAP chimera polypeptide-encoding nucleic acid molecule of interest.

Percent nucleic acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=1515, multi-pass e-value 0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, ML-IAP chimera variant polynucleotides are nucleic acid-molecules that encode an active ML-IAP chimera polypeptide and which are capable of hybridizing, preferably under stringent hybridization and wash conditions, to nucleotide sequences encoding a full-length ML-IAP chimera polypeptide as disclosed herein. ML-IAP chimera variant polypeptides may be those that are encoded by a ML-IAP chimera variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the ML-IAP chimera polypeptide natural environment will not be present. Ordinarily, however, isolated polypeptide will be prepared by at least one purification step.

An "isolated" ML-IAP chimera polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-ML-IAP chimera monoclonal antibodies (including agonist, antagonist, and neutralizing antibodies), anti-ML-IAP chimera antibody compositions with polyepitopic specificity, single chain anti-ML-IAP chimera antibodies, and fragments of anti-ML-IAP chimera antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficol/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and %SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a ML-IAP chimera polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a ML-IAP chimera polypeptide which retain a biological and/or an immunological activity of native or naturally-occurring IAP polypeptide, wherein "biological" activity refers to a biological function (either inhibitory or stimulatory) caused by a native or naturally-occurring IAP polypeptide other than the ability to induce the production of an antibody against an antigenic epitope possessed by a native or naturally-occurring IAP polypeptide and an "immunological" activity refers to the ability to induce the production of an antibody against an antigenic epitope possessed by a native or naturally-occurring IAP polypeptide.

The term "antagonist" is used in the broadest sense, and includes any molecule that partially or fully blocks, inhibits, or neutralizes a biological activity of a ML-IAP chimera polypeptide disclosed herein. In a similar manner, the term "agonist" is used in the broadest sense and includes any molecule that mimics a biological activity of a ML-IAP chimera polypeptide disclosed herein. Suitable agonist or antagonist molecules specifically include agonist or antagonist antibodies or antibody fragments, fragments or amino acid sequence variants of native IAP polypeptides, peptides, antisense oligonucleotides, small organic molecules, etc. Methods for identifying agonists or antagonists of a ML-IAP chimera polypeptide may comprise contacting a ML-IAP chimera polypeptide with a candidate agonist or antagonist molecule and measuring a detectable change in one or more biological activities normally associated with the ML-IAP chimera polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a MLIAP chimera polypeptide or antibody thereto) to a mammal. The components of the liposome are commonly arranged in a bilayer formation, similar to the lipid arrangement of biological membranes.

The term "epitope tagged" when used herein refers to a chimeric oligopeptide comprising a IAP inhibitor fused to a "tag polypeptide". The tag polypeptide has enough residues to provide an epitope against which an antibody can be made, yet is short enough such that it does not interfere with activity of the oligopeptide to which it is fused. The tag polypeptide preferably also is fairly unique so that the antibody does not substantially cross-react with other epitopes. Optionally, the tag polypeptide is a carrier polypeptide that allows entry of the chimeric IAP inhibitor into cells or is a proteinaceous toxin capable of inhibiting cell growth. Suitable tag polypeptides generally have at least six amino acid residues and usually between about 8 and 50 amino acid residues (preferably, between about 10 and 20 amino acid residues).

"IAP inhibitors" are molecules that block the anti-apoptotic activity of Inhibitor of Apoptosis Proteins (IAP). Examples of naturally occuring IAP inhibitors are the Smac/DIABLO proteins in mammals, and the HID, RPR and GRIM proteins in *Drosophila*.

"Active inhibitor" for the purposes herein refers to form(s) of an IAP inhibitor which retains a biological activity of native or naturally-occurring IAP inhibitors, wherein "biological" activity refers to a biological function caused by a native or naturally-occurring IAP inhibitor.

"IAPs" or Inhibitors of Apoptosis Proteins are molecules that inhibit apoptosis of a cell by physically interacting with, and blocking the action of, caspase molecules within the apoptosis pathway. Examples of IAP molecules are ML-IAP (Accession Number: BIR7_HUMAN), XIAP, NAIP, C-IAP1 and C-IAP2. Structurally, IAPs contain one or more BIR domains and most contain a carboxy terminal RING finger domain.

"Caspase" is defined as a cysteine protease polypeptide that cleaves polypeptide substrates on the C-terminal side of Aspartic acid residues.

"BIR domain" (Baculovirus IAP Repeat) is a polypeptide that contains a protein structure that is capable of specifically binding to and inhibiting, a caspase. Specifically, the BIR domain of ML-IAP is defined by amino acids 87–168 of the sequence disclosed in Accession Number: BIR7_HUMAN.

The term "antagonist" is used in the broadest sense, and includes any molecule that partially or fully blocks, inhibits, or neutralizes a biological activity of an IAP polypeptide. In a similar manner, the term "agents" is used in the broadest sense and includes any molecule that mimics a biological activity of a native IAP polypeptide inhibitor. Suitable agents or antagonist molecules specifically include oligopeptides and small organic molecules. Methods for identifying antagonists of an IAP polypeptide may comprise contacting an IAP polypeptide with a candidate antagonist molecule and measuring a detectable change in one or more biological activities normally associated with the IAP polypeptide.

"Oligopeptides" are short amino acid sequences between 3 and 30 amino acid residues in length and encompass naturally occurring amino acid residues and non-naturally occurring analogs of residues which may be used singly or in combination with naturally occurring amino acid residues in order to give the oligopeptide a particular conformational specificity or a particular biological activity, such as resistance to proteolysis.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an IAP polypeptide-expressing cancer if, after receiving a therapeutic amount of an IAP inhibitor according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer, reduced morbidity and mortality, and improvement in quality of life issues. To the extent the IAP inhibitor may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal; including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which a ML-IAP chimera of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant, which is useful for delivery of a drug (such as an IAP inhibitor) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of an IAP inhibitor as disclosed herein is an amount sufficient to carry out a specifically stated purpose. An "effective amount" may be determined empirically and in a routine manner, in relation to the stated purpose.

The term "therapeutically effective amount" refers to an amount of a IAP inhibitor or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an IAP inhibitor is an amount capable of inhibiting the growth of a cell, especially tumor, e.g., cancer cell, either in vitro or in vivo. A "growth inhibitory amount" of an IAP inhibitor for purposes of inhibiting neoplastic cell growth may be determined empirically and in a routine manner.

A "cytotoxic amount" of an IAP inhibitor is an amount capable of causing the destruction of a cell, especially tumor, e.g., cancer cell, either in vitro or in vivo. A "cytotoxic amount" of an IAP inhibitor for purposes of inhibiting neoplastic cell growth may be determined empirically and in a routine manner.

IAP inhibitors that are oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998–4002 (1984); Geysen et al., Proc. Natl. Acad. Sci. U.S.A., 82:178–182 (1985); Geysen et al., in Synthetic Peptides as Antigens, 130–149 (1986); Geysen et al., J. Immunol. Meth., 102:259–274 (1987); Schoofs et al., J. Immunol., 140:611–616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

An IAP inhibitor that is an organic molecule other than an oligopeptide or antibody as defined herein that binds, preferably specifically, to an IAP polypeptide or IAP chimera as described herein. IAP inhibitors that are organic molecules may be identified and chemically synthesized using known methodology (see, e.g., PCT Publication Nos. WO00/00823 and WO00/39585). Small organic molecules are usually less than about 2000 Daltons in size, alternatively less than about 1500, 750, 500, 250 or 200 Daltons in size, wherein such organic molecules that are capable of binding, preferably specifically, to an IAP polypeptide as described herein may be identified without undue experimentation using well known techniques. In this regard, it is noted that techniques for screening organic molecule libraries for molecules that are capable of binding to a polypeptide target are well known in the art (see, e.g., PCF Publication Nos. WO00/00823 and WO00/39585).

An IAP inhibitor "which binds" an IAP, polypeptide of interest, e.g. a tumor-associated polypeptide target, is one that binds the BIR domain with sufficient affinity such that the IAP inhibitor is useful as a diagnostic and/or therapeutic agent in targeting a cell or tissue expressing the IAP polypeptide, and does not significantly cross-react with other proteins. In such embodiments, the extent of binding of the IAP inhibitor to a "non-target" protein will be less than about 10% of the binding of the IAP inhibitor to its particular target protein as determined by fluorescence polarization, fluorescence activated cell sorting (FACS) analysis or radioimmunoprecipitation (RIA). With regard to the binding of an IAP inhibitor to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An IAP inhibitor that "inhibits the growth of tumor cells expressing an IAP polypeptide" or a "growth inhibitory" IAP inhibitor is one which results in measurable growth inhibition of cancer cells expressing or overexpressing the appropriate IAP polypeptide. Preferred growth inhibitory IAP inhibitors inhibit growth of BIR domain containing IAPs expressed in tumor cells by greater than 20%, preferably from about 20% to about 50%, and even more preferably, by greater than 50% (e.g., from about 50% to about 100%) as compared to the appropriate control, the control typically being tumor cells not treated with the IAP inhibitor being tested. Growth inhibition of tumor cells in vivo can be determined in various ways such as is described in the Experimental Examples section below.

An IAP inhibitor which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is a tumor cell, e.g., a prostate, breast, ovarian, stomach, endometrial, lung, kidney, colon, melanoma or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the IAP inhibitor which induces apoptosis is one which results in about 2 to 50 fold, preferably about 5 to 50 fold, and most preferably about 10 to 50 fold, induction of annexin binding relative to untreated cell in an annexin binding assay.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

A "IAP polypeptide-expressing cell" is a cell which expresses an endogenous or transfected IAP polypeptide. An "IAP polypeptide-expressing cancer" is a cancer comprising cells that have an IAP polypeptide present. An "IAP polypeptide-expressing cancer" optionally produces sufficient levels of IAP polypeptide in cells thereof, such that an IAP inhibitor can bind thereto and have a therapeutic effect with respect to the cancer. In another embodiment, an "IAP polypeptide expressing cancer" optionally produces sufficient levels of IAP polypeptide, such that an IAP inhibitor antagonist can bind thereto and have a therapeutic effect with respect to the cancer. A cancer that "overexpresses" an IAP polypeptide is one that has significantly higher levels of IAP polypeptide in the cell, compared to a noncancerous cell of the same tissue type. Such overexpression may be caused by gene amplification or by increased transcription or translation. IAP polypeptide overexpression may be determined in a diagnostic or prognostic assay by evaluating increased levels of the IAP protein present in a cell, (e.g., via an immunohistochemistry assay using anti-IAP polypeptide antibodies prepared against an isolated IAP polypeptide which may be prepared using recombinant DNA technology from an isolated nucleic acid encoding the IAP polypeptide; FACS analysis, etc.). Alternatively, or additionally, one may measure levels of IAP polypeptide-encoding nucleic acid or mRNA in the cell, e.g., via fluorescent in situ hybridization using a nucleic acid based probe corresponding to an IAP-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study IAP polypeptide overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued March 28, 1995; and Sias et al., *J. Immunol. Methods* 132:73–80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

The word "label" when used herein refers to a detectable compound or composition that is conjugated directly or indirectly to the putative IAP inhibitor or ML-IAP chimera so as to generate a "labeled" molecule. The label may be detectable by itself (e.g. radioisotope labels or fluorescent labels) or, in the case of an enzymatic label, may catalyze chemical alteration of a substrate compound or composition that is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially an IAP polypeptide-expressing cancer cell, either in vitro or in vivo. Thus, the growth inhibitory agent may be one which significantly reduces the percentage of IAP-expressing cells in S phase. Examples of growth inhibitory agents include agents that block cell cycle progression (at a place other than S phase), such as agents that induce G1 arrest and M-phase arrest Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2, 3,6-trideoxy-α-L-lyxo-hexapyranosyl)oxy]-7,8,9,10-tetrahydro-6,8,11-trihydroxy-8-(hydroxyacetyl)-1-methoxy-5, 12-naphthacenedione.

The term "cytokine" is a generic term for proteins released by one cell population that act on another cell as intercellular mediators. Examples of such cytokines are lympholines, monokines, and traditional polypeptide hormones. Included among the cytokines are growth hormone such as human growth hormone, N-methionyl human growth hormone, and boyine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon -α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

TABLE 1

```
/*
 *
 * C-C increased from 12 to 15
 * Z is average of EQ
 * B is average of ND
 * match with stop is _M; stop-stop = 0; J (joker) match = 0
 */
#define _M      -8      /* value of a match with a stop */
int     _day[26][26] = {
/*      A B C D E F G H I J K L M N O P Q R S T U V W X Y Z */
/* A */ {2, 0, -2, 0, 0, -4, 1, -1, -1, 0, -1, -2, -1, 0, _M, 1, 0, -2, 1, 1, 0, 0, -6, 0, -3, 0},
/* B */ {0, 3, -4, 3, 2, -5, 0, 1, -2, 0, 0, -3, -2, 2, _M, -1, 1, 0, 0, 0, 0, -2, -5, 0, -3, 1},
/* C */ {-2, -4, 15, -5, -5, -4, -3, -3, -2, 0, -5, -6, -5, -4, _M, -3, -5, -4, 0, -2, 0, -2, -8, 0, 0, -5},
/* D */ {0, 3, -5, 4, 3, -6, 1, 1, -2, 0, 0, -4, -3, 2, _M, -1, 2, -1, 0, 0, 0, -2, -7, 0, -4, 2},
/* E */ {0, 2, -5, 3, 4, -5, 0, 1, -2, 0, 0, -3, -2, 1, _M, -1, 2, -1, 0, 0, 0, -2, -7, 0, -4, 3},
/* F */ {-4, -5, -4, -6, -5, 9, -5, -2, 1, 0, -5, 2, 0, -4 , _M, -5, -5, -4, -3, -3, 0, -1, 0, 0, 7, -5},
/* G */ {1 , 0, -3, 1, 0, -5, 5, -2, -3, 0, -2, -4, -3, 0, _M, -1 , -1, -3, 1, 0, 0, -1, -7, 0, -5, 0},
/* H */ {-1 , 1, -3, 1, 1, -2, -2, 6, -2, 0, 0, -2, -2, 2, _M, 0, 3, 2, -1, -1, 0, -2, -3, 0, 0, 2},
/* I */ {-1, -2, -2, -2, -2, 1, -3, -2, 5, 0, -2, 2, 2, -2, _M, -2, -2, -2, -1, 0, 0, 4, -5, 0, -1, -2},
/* J */ {0, 0, 0, 0, 0, 0, 0, 0, 0, 0, 0, 0, 0, 0, _M, 0, 0, 0, 0, 0, 0, 0, 0, 0, 0, 0},
/* K */ {-1, 0, -5, 0, 0, -5, -2, 0, -2, 0, 5, -3, 0, 1, _M, -1, 1, 3, 0, 0, 0, -2, -3, 0, -4, 0},
/* L */ {-2, -3, -6, -4, -3, 2, -4, -2, 2, 0, -3, 6, 4, -3, _M, -3, -2, -3, -3, -1, 0, 2, -2, 0, -1, -2},
/* M */ {-1, -2, -5, -3, -2, 0, -3, -2, 2, 0, 0, 4, 6, -2, _M, -2, -1 , 0, -2, -1, 0, 2, -4, 0, -2, -1},
/* N */ {0, 2, -4, 2, 1, -4, 0, 2, -2, 0, 1, -3, -2, 2, _M, -1, 1, 0, 1, 0, 0, -2, -4, 0, -2, 1},
/* O */ {_M, _M, _M, _M, _M, _M, _M, _M, _M, _M, _M, _M, _M, _M, 0, _M, _M, _M, _M, _M, _M, _M, _M, _M, _M,
         _M},
/* P */ {1, -1, -3, -1, -1, -5, -1, 0, -2, 0, -1, -3, -2, -1, _M, 6, 0, 0, 1, 0, 0, -1, -6, 0, -5, 0},
/* Q */ {0, 1, -5, 2, 2, -5, -1, 3, -2, 0, 1, -2, -1, 1, _M, 0, 4, 1, -1, -1, 0, -2, -5, 0, -4, 3},
/* R */ {-2, 0, -4, -1, -1, -4, -3, 2, -2, 0, 3, -3, 0, 0, _M, 0, 1, 6, 0, -1, 0, -2, 2, 0, -4, 0},
/* S */ {1, 0, 0, 0, 0, -3, 1, -1, -1, 0, 0, -3, -2, 1, _M, 1, -1, 0, 2, 1, 0, -1, -2, 0, -3, 0},
/* T */ {1, 0, -2, 0, 0, -3, 0, -1, 0, 0, 0, -1, -1, 0, _M, 0, -1, -1, 1, 3, 0, 0, -5, 0, -3, 0},
/* U */ {0, 0, 0, 0, 0, 0, 0, 0, 0, 0, 0, 0, 0, 0, _M, 0, 0, 0, 0, 0, 0, 0, 0, 0, 0, 0},
/* V */ {0, -2, -2, -2, -2, -1, -1, -2, 4, 0, -2, 2, 2, -2, _M, -1 , -2, -2, -1, 0, 0, 4, -6, 0, -2, -2},
/* W */ {-6, -5, -8, -7, -7, 0, -7, -3, -5, 0, -3, -2, -4, -4, _M, -6, -5, 2, -2, -5, 0, -6, 17, 0, 0, -6},
/* X */ {0, 0, 0, 0, 0, 0, 0, 0, 0, 0, 0, 0, 0, 0, _M, 0, 0, 0, 0, 0, 0, 0, 0, 0, 0, 0},
/* Y */ {-3, -3, 0, -4, -4, 7, -5, 0, -1, 0, -4, -1 , -2, -2, _M, -5, -4, -4, -3, -3, 0, -2, 0, 0, 10, -4},
/* Z */ {0, 1, -5, 2, 3, -5, 0, 2, -2, 0, 0, -2, -1, 1, _M, 0, 3, 0, 0, 0, 0, -2, -6, 0, -4, 4}
};
/*
 */
#include <stdio.h>
#include <ctype.h>
#define MAXJMP      16          /* max jumps in a diag */
#define MAXGAP      24          /* don't continue to penalize gaps larger than this */
#define JMPS        1024        /* max jmps in an path */
#define MX          4           /* save if there's at least MX-1 bases since last jmp */
#define DMAT        3           /* value of matching bases */
#define DMIS        0           /* penalty for mismatched bases */
#define DINS0       8           /* penalty for a gap */
#define DINS1       1           /* penalty per base */
#define PINS0       8           /* penalty for a gap */
#define PINS1       4           /* penalty per residue */
struct jmp {
    short           n[MAXJMP];          /* size of jmp (neg for dely) */
    unsigned short  x[MAXJMP];          /* base no. of jmp in seq x */
};                                      /* limits seq to 2^16 -1 */
struct diag {
    int             score;              /* score at last jmp */
    long            offset;             /* offset of prev block */
    short           ijmp;               /* current jmp index */
    struct jmp      jp;                 /* list of jmps */
};
struct path {
    int             spc;                /* number of leading spaces */
```

TABLE 1-continued

```
    short       n[JMPS];/* size of jmp (gap) */
    int         x[JMPS];/* loc of jmp (last elem before gap) */
};
char        *ofile;                         /* output file name */
char        *namex[2];                      /* seq names: getseqs( ) */
char        *prog;                          /* prog name for err msgs */
char        *seqx[2];                       /* seqs: getseqs( ) */
int         dmax;                           /* best diag: nw( ) */
int         dmax0;                          /* final diag */
int         dna;                            /* set if dna: main( ) */
int         endgaps;                        /* set if penalizing end gaps */
int         gapx, gapy;                     /* total gaps in seqs */
int         len0, len1;                     /* seq lens */
int         ngapx, ngapy;                   /* total size of gaps */
int         smax;                           /* max score: nw( ) */
int         *xbm;                           /* bitmap for matching */
long        offset;                         /* current offset in jmp file */
struct diag *dx;                            /* holds diagonals */
struct path pp[2];                          /* holds path for seqs */
char        *calloc( ), *malloc( ), *index( ), *strcpy( );
char        *getseq( ), *g_calloc( );
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static _dbval[26] = {
    1,14,2,13,0,0,4,11,0,0,12,0,3,15,0,0,0,5,6,8,8,7,9,0,10,0
};
static _pbval[26] = {
    1, 2|(1<<('D'-'A'))|(1<<('N'-'A')), 4, 8, 16, 32, 64,
    128, 256, 0xFFFFFFFF, 1<<10, 1<<11, 1<<12, 1<<13, 1<<14,
    1<<15, 1<<16, 1<<17, 1<<18, 1<<19, 1<<20, 1<<21, 1<<22,
    1<<23, 1<<34, 1<<25|(1<<('E'-'A'))|(1<<('Q'-'A'))
};
main(ac, av)                                                                    main
    int     ac;
    char    *av[ ];
{
    prog = av[0];
    if(ac != 3) {
        fprintf(stderr, "usage: %s file1 file2\n", prog);
        fprintf(stderr, "where file1 and file2 are two dna or two protein sequences.\n");
        fprintf(stderr, "The sequences can be in upper- or lower-case\n");
        fprintf(stderr, "Any lines beginning with ';' or '<' are ignored\n");
        fprintf(stderr, "Output is in the file \"align.out\"\n");
        exit(1);
    }
    namex[0] = av[1];
    namex[1] = av[2];
    seqx[0] = getseq(namex[0], &len0);
    seqx[1] = getseq(namex[1], &len1);
    xbm = (dna)? _dbval : _pbval;
    endgaps = 0;                        /* 1 to penalize endgaps */
    ofile = "align.out";                /* output file */
    nw( );                              /* fill in the matrix, get the possible jmps */
    readjmps( );                        /* get the actual jmps */
    print( );                           /* print stats, alignment */
    cleanup(0);                         /* unlink any tmp files */}
/* do the alignment, return best score: main( )
* dna: values in Fitch and Smith, PNAS, 80, 1382–1386, 1983
* pro: PAM 250 values
* When scores are equal, we prefer mismatches to any gap, prefer
* a new gap to extending an ongoing gap, and prefer a gap in seqx
* to a gap in seq y.
*/
nw( )                                                                           nw
{
    char    *px, *py;                   /* seqs and ptrs */
```

TABLE 1-continued

```
    int         *ndely, *dely;         /* keep track of dely */
    int         ndelx, delx;           /* keep track of delx */
    int         *tmp;                  /* for swapping row0, row1 */
    int         mis;                   /* score for each type */
    int         ins0, ins1;            /* insertion penalties */
    register    id;                    /* diagonal index */
    register    ij;                    /* jmp index */
    register    *col0, *col1;          /* score for curr, last row */
    register    xx, yy;                /* index into seqs */
    dx = (struct diag *)g_calloc("to get diags", len0+len1+1, sizeof(struct diag));
    ndely = (int *)g_calloc("to get ndely", len1+1, sizeof(int));
    dely = (int *)g_calloc("to get dely", len1+1, sizeof(int));
    col0 = (int *)g_calloc("to get col0", len1+1, sizeof(int));
    col1 = (int *)g_calloc("to get col1", len1+1, sizeof(int));
    ins0 = (dna)? DINS0 : PINS0;
    ins1 = (dna)? DINS1 : PINS1;
    smax = -10000;
    if (endgaps) {
        for (col0[0] = dely[0] = -ins0, yy = 1; yy <= len1; yy++) {
            col0[yy] = dely[yy] = col0[yy-1] - ins1;
            ndely[yy] = yy;
        }
        col0[0] = 0;         /* Waterman Bull Math Biol 84 */
    }
    else
        for (yy = 1; yy <= len1; yy++)
            dely[yy] = -ins0;
    /* fill in match matrix
     */
    for (px = seqx[0], xx = 1; xx <= len0; px++, xx++) {
        /* initialize first entry in col
         */
        if (endgaps) {
            if(xx == 1)
                col1[0] = delx = -(ins0+ins1);
            else
                col1[0] = delx = col0[0] - ins1;
            ndelx = xx;
        }
        else {
            col1[0] = 0;
            delx = -ins0;
            ndelx = 0;
        }
                                                                                    ... nw
        for (py = seqx[1], yy = 1; yy <= len1; py++, yy++) {
            mis = col0[yy-1];
            if (dna)
                mis += (xbm[*px-'A']&xbm[*py-'A'])? DMAT : DMIS;
            else
                mis += _day[*px-'A'][*py-'A'];
            /* update penalty for del in x seq;
             * favor new del over ongong del
             * ignore MAXGAP if weighting endgaps
             */
            if (endgaps || ndely[yy] < MAXGAP) {
                if (col0[yy] - ins0 >= dely[yy]) {
                    dely[yy] = col0[yy] - (ins0+ins1);
                    ndely[yy] = 1;
                } else {
                    dely[yy] -= ins1;
                    ndely[yy]++;
                }
            } else {
                if (col0[yy] - (ins0+ins1) >= dely[yy]) {
                    dely[yy] = col0[yy] - (ins0+ins1);
                    ndely[yy] = 1;
                } else
                    ndely[yy]++;
            }
            /* update penalty for del in y seq;
             * favor new del over ongong del
             */
            if (endgaps || ndelx < MAXGAP) {
                if (col1[yy-1] - ins0 >= delx) {
                    delx = col1[yy-1] - (ins0+ins1);
                    ndelx = 1;
                } else {
                    delx -= ins1;
```

TABLE 1-continued

```
                    ndelx++;
                }
            } else {
                if (col1[yy-1] - (ins0+ins1) >= delx) {
                    delx = col1[yy-1] - (ins0+ins1);
                    ndelx = 1;
                } else
                    ndelx++;
            }
            /* pick the maximum score; we're favoring
             * mis over any del and delx over dely
             */
            id = xx - yy + len1 - 1;                                                                    . . . nw
            if (mis >= delx && mis >= dely[yy])
                col1[yy] = mis;
            else if (delx >= dely[yy]) {
                col1[yy] = delx;
                ij = dx[id].ijmp;
                if (dx[id].jp.n[0] && (!dna || (ndelx >= MAXJMP
                    && xx > dx[id].jp.x[ij]+MX) || mis > dx[id].score+DINS0)) {
                        dx[id].ijmp++;
                        if (++ij >= MAXJMP) {
                            writejmps(id);
                            ij = dx[id].ijmp = 0;
                            dx[id].offset = offset;
                            offset += sizeof(struct jmp) + sizeof(offset);
                        }
                }
                dx[id].jp.n[ij] = ndelx;
                dx[id].jp.x[ij] = xx;
                dx[id].score = delx;
            }
            else {
                col1[yy] = dely[yy];
                ij = dx[id].ijmp;
if (dx[id].jp.n[0] && (!dna || (ndely[yy] >= MAXJMP
                    && xx > dx[id].jp.x[ij]+MX) || mis > dx[id].score+DINS0)) {
                        dx[id].ijmp++;
                        if (++ij >= MAXJMP }
                            writejmps(id);
                            ij = dx[id].ijmp = 0;
                            dx[id].offset = offset;
                            offset += sizeof(struct jmp) + sizeof(offset);
                        }
                }
                dx[id].jp.n[ij] = -ndely[yy];
                dx[id].jp.x[ij] = xx;
                dx[id].score = dely[yy];
            }
            if (xx == len0 && yy < len1) {
                /* last col
                 */
                if (endgaps)
                    col1[yy] -= ins0+ins1 *(len1-yy);
                if (col1[yy] > smax) {
                    smax = col1[yy];
                    dmax = id;
                }
            }
        }
        if (endgaps && xx < len0)
            col1[yy-1] -= ins0+ins1*(len0-xx);
        if (col1[yy-1] > smax) {
            smax = col1[yy-1];
            dmax = id;
        }
        tmp = col0; col0 = col1; col1 = tmp;         }
(void) free((char *)ndely);
(void) free((char *)dely);
(void) free((char *)col0);
(void) free((char *)col1);            }
/*
 *
 * print( ) -- only routine visible outside this module
 *
 * static:
 * getmat( ) -- trace back best path, count matches: print( )
 * pr_align( ) -- print alignment of described in array p[ ]: print( )
```

TABLE 1-continued

```
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
#define SPC         3
#define P_LINE      256         /* maximum output line */
#define P_SPC       3           /* space between name or num and seq */
extern              _day[26][26];
int                 olen;       /* set output line length */
FILE                *fx;        /* output file */
print( )                                                                                print
}
        int     lx, ly, firstgap, lastgap;      /* overlap */
        if ((fx = fopen(ofile, "w")) == 0) {
                fprintf(stderr, "%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1){          /* trailing gap in x */
                lastgap = len0 - dmax0 - 1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align( );            }
/*
* trace back the best path, count matches
*/
static
getmat(lx, ly, firstgap, lastgap)                                                       getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;
        /* get total matches, score
        */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
```

TABLE 1-continued

```
            if (n0++ == pp[0].x[i0])
                siz0 = pp[0].n[i0++];
            if(n1++ == pp[1].x[i1])
                siz1 = pp[1].n[i1 ++];
            p0++;
            p1++;
        }
    }
    /* pct homology:
     * if penalizing endgaps, base is the shorter seq
     * else, knock off overhangs and take shorter core
     */
    if (endgaps)
        lx = (len0 < len1)? len0 : len1;
    else
        lx = (lx < ly)? lx : ly;
    pct = 100.*(double)nm/(double)lx;
    fprintf(fx, "\n");
    fprintf(fx, "<%d match%s in an overlap of %d: %.2f percent similarity\n",
        nm, (nm == 1)? " ": "es", lx, pct);
    fprintf(fx, "<gaps in first sequence: %d", gapx);                                              . . . getmat
    if (gapx) {
        (void) sprintf(outx, "(%d %s%s)",
            ngapx, (dna)? "base":"residue", (ngapx == 1)? " ":"s");
        fprintf(fx, "%s", outx);
    }
    fprintf(fx, ", gaps in second sequence: %d", gapy);
    if (gapy) {
        (void) sprintf(outx, "(%d %s%s)",
            ngapy, (dna)? "base":"residue", (ngapy == 1)? " ":"s");
        fprintf(fx, "%s", outx);
    }
    if (dna)
        fprintf(fx,
            "\n<score: %d (match = %d, mismatch = %d, gap penalty = %d + %d per base)\n",
            smax, DMAT, DMIS, DINS0, DINS1);
    else
        fprintf(fx,
            "\n<score: %d (Dayhoff PAM 250 matrix, gap penalty = %d + %d per residue)\n",
            smax, PINS0, PINS1);
    if (endgaps)
        fprintf(fx,
            "<endgaps penalized. left endgap: %d %s%s, right endgap: %d %s%s\n",
            firstgap, (dna)? "base" : "residue", (firstgap == 1)? " " : "s",
            lastgap, (dna)? "base" : "residue", (lastgap == 1)? " " : "s");
    else
        fprintf(fx, "<endgaps not penalized\n");
}
static      nm;              /* matches in core -- for checking */
static      lmax;            /* lengths of stripped file names */
static      ij[2];           /* jmp index for a path */
static      nc[2];           /* number at start of current line */
static      ni[2];           /* current elem number -- for gapping */
static      siz[2];
static char *ps[2];          /* ptr to current element */
static char *po[2];          /* ptr to next output char slot */
static char out[2][P_LINE];  /* output line */
static char star[P_LINE];    /* set by stars( ) */
/*
 * print alignment of described in struct path pp[ ]
 */
static
pr_align( )                                                                                        pr_align
{
    int           nn;        /* char count */
    int           more;
    register      i;
    for (i = 0, lmax = 0; i < 2; i++) {
        nn = stripname(namex[i]);
        if (nn > lmax)
            lmax = nn;
        nc[i] = 1;
        ni[i] = 1;
        siz[i] = ij[i] = 0;
        ps[i] = seqx[i];
        po[i] = out[i];         }
    for (nn = nm = 0, more = 1; more;) {                                                           . . . pr_align
        for (i = more = 0; i < 2; i++) {
            /*
             * do we have more of this sequence?
```

TABLE 1-continued

```
            */
            if (!*ps[i])
                continue;
            more++;
            if (pp[i].spc) {           /* leading space */
                *po[i]++ = ' ';
                pp[i].spc--;
            }
            else if (siz[i]) {         /* in a gap */
                *po[i]++ = '-';
                siz[i]--;
            }
            else {                     /* we're putting a seq element
                                        */
                *po[i] = *ps[i];
                if (islower(*ps[i]))
                    *ps[i] = toupper(*ps[i]);
                po[i]++;
                ps[i]++;
                /*
                 * are we at next gap for this seq?
                 */
                if (ni[i] == pp[i].x[ij[i]]) {
                    /*
                     * we need to merge all gaps
                     * at this location
                     */
                    siz[i] = pp[i].n[ij[i]++];
                    while (ni[i] == pp[i].x[ij[i]])
                        siz[i] += pp[i].n[ij[i]++];
                }
                ni[i]++;
            }
        }
        if (++nn == olen || !more && nn) {
            dumpblock( );
            for (i = 0; i < 2; i++)
                po[i] = out[i];
            nn = 0;
        }
    }
}
/*
 * dump a block of lines, including numbers, stars: pr_align( )
 */
static
dumpblock( )                                                                    dumpblock
{
    register i;
    for (i = 0; i < 2; i++)
        *po[i]-- = '\0';
                                                                                ... dumpblock
    (void) putc('\n', fx);
    for (i = 0; i < 2; i++) {
        if (*out[i] && (*out[i] !=' ' || *(po[i]) != ' ')) {
            if (i == 0)
                nums(i);
            if (i == 0 && *out[1])
                stars( );
            putline(i);
            if (i == 0 && *out[1])
                fprintf(fx, star);
            if (i == 1)
                nums(i);
        }
    }
}
/*
 * put out a number line: dumpblock( )
 */
static
nums(ix)                                                                        nums
    int       ix;        /* index in out[ ] holding seq line */
{
    char              nline[P_LINE];
    register          i, j;
    register char     *pn, *px, *py;
    for (pn = nline, i = 0; i < lmax+P_SPC; i++, pn++)
        *pn = ' ';
```

TABLE 1-continued

```
        for (i = nc[ix], py = out[ix]; *py; py++, pn++) {
            if (*py == ' ' || *py == '-')
                *pn = ' ';
            else {
                if (i% 10 == 0 || (i == 1 && nc[ix] != 1)) {
                    j = (i < 0)? -i : i;
                    for (px = pn; j; j /= 10, px--)
                        *px = j% 10 + '0';
                    if (i < 0)
                        *px = '-';
                }
                else
                    *pn = ' ';
                i++;
            }
        }
        *pn = '\0';
        nc[ix] = i;
        for (pn = nline; *pn; pn++)
            (void) putc(*pn, fx);
        (void) putc('\n', fx);
}
/*
* put out a line (name, [num], seq. [num]): dumpblock( )
*/
static
putline(ix)                                                              putline
    int         ix;         {
                                                                         . . . putline
    int         i;
    register char   *px;
    for (px = namex[ix], i = 0; *px && *px != ':'; px++, i++)
        (void) putc("px, fx);
    for (; i <lmax+P_SPC; i++)
        (void) putc(' ', fx);
    /* these count from 1:
    * ni[ ] is current element (from 1)
    * nc[ ] is number at start of current line
    */
    for (px = out[ix]; *px; px++)
        (void) putc(*px&0x7F, fx);
    (void) putc('\n', fx);
}
/*
* put a line of stars (seqs always in out[0], out[1]): dumpblock( )
*/
static
stars( )                                                                 stars
{
    int         i;
    register char   *p0, *p1, cx, *px;
    if (!*out[0] || (*out[0] ==' ' && *(po[0]) == ' ') ||
        !*out[1] || (*out[1] ==' ' && *(po[1]) == ' '))
        return;
    px = star;
    for (i = lmax+P_SPC; i; i--)
        *px++ = ' ';
    for (p0 = out[0], p1 = out[1]; *p0 && *p1; p0++, p1++) {
        if (isalpha(*p0) && isalpha(*p1)) {
            if (xbm[*p0-'A']&xbm[*p1-'A']) {
                cx = '*';
                nm++;
            }
            else if (!dna && __day[*p0-'A'][*p1-'A'] > 0)
                cx = '.';
            else
                cx = ' ';
        }
        else
            cx = ' ';
        *px++ = cx;
    }
    *px++ = '\n';
    *px = '\0';
}
/*
* strip path or prefix from pn, return len: pr_align( )
*/
static
```

TABLE 1-continued

```
stripname(pn)                                                                                           stripname
      char       *pn;         /* file name (may be path) */
{
      register char       *px, *py;
      py = 0;
      for (px = pn; *px; px++)
          if (*px == '/')
              py = px + 1;
      if (py)
          (void) strcpy(pn, py);
      return(strlen(pn));
}
/*
* cleanup( ) -- cleanup any tmp file
* getseq( ) -- read in seq, set dna, len, maxlen
* g_calloc( ) -- calloc( ) with error checkin
* readjmps( ) -- get the good jmps, from tmp file if necessary
* writejmps( ) -- write a filled array of jmps to a tmp file: nw( )
*/
#include "nw.h"
#include <sys/file.h>
char       *jname = "/tmp/homgXXXXXX";        /* tmp file for jmps */
FILE       *fj;
int        cleanup( );                         /* cleanup tmp file */
long       lseek( );
/*
* remove any tmp file if we blow
*/
cleanup(i)                                                                                              cleanup
      int        i;
{
      if (fj)
          (void) unlink(jname);
      exit(i);
}
/*
* read, return ptr to seq, set dna, len, maxlen
* skip lines starting with ';', '<', or '>'
* seq in upper or lower case
*/
char       *
getseq(file, len)                                                                                       getseq
      char    *file;        /* file name */
      int     *len;         /* seq len */
{
      char             line[1024], *pseq;
      register char    *px, *py;
      int              natgc, tlen;
      FILE             *fp;
      if ((fp = fopen(file, "r")) == 0) {
          fprintf(stderr, "%s: can't read %s\n", prog, file);
          exit(1);
      }
      tlen = natgc = 0;
      while (fgets(line, 1024, fp)) {
          if ( *line == ';' || *line == '<' || *line == '>')
              continue;
          for (px = line; *px != '\n'; px++)
              if (isupper(*px) || islower(*px))
                  tlen++;
      }
      if ((pseq = malloc((unsigned)(tlen+6))) == 0) {
          fprintf(stderr, "%s: malloc( ) failed to get %d bytes for %s\n", prog, tlen+6, file);
          exit(1);
      }
      pseq[0] = pseq[1] = pseq[2] = pseq[3] = '\0';
                                                                                                        . . . getseq
      py = pseq + 4;
      *len = tlen;
      rewind(fp);
      while (fgets(line, 1024, fp)) {
          if ( *line == ';' || *line == '<' || *line == '>')
              continue;
          for (px = line; *px != '\n'; px++) {
              if (isupper(*px))
                  *py++ = *px;
              else if (islower(*px))
                  *py++ = toupper(*px);
              if (index("ATGCU",*(py-1)))
```

TABLE 1-continued

```
                    natgc++;
            }
    }
    *py++ = '\0';
    *py = '\0';
    (void) fclose(fp);
    dna = natgc > (tlen/3);
    return(pseq+4);
}
char *
g_calloc(msg, nx, sz)                                                                                    g_calloc
        char        *msg;           /* program, calling routine */
        int         nx, sz;         /* number and size of elements */
{
        char            *px, *calloc( );
        if ((px = calloc((unsigned)nx, (unsigned)sz)) == 0) {
            if (*msg) {
                fprintf(stderr, "%s: g_calloc( ) failed %s (n=%d, sz=%d)\n", prog, msg, nx, sz);
                exit(1);
            }
        }
        return(px);
}
/*
 * get final jmps from dx[ ] or tmp file, set pp[ ], reset dmax: main( )
 */
readjmps( )                                                                                              readjmps
{
        int             fd = -1;
        int             siz, i0, i1;
        register i, j, xx;
        if (fj) {
            (void) fclose(fj);
            if ((fd = open(jname, O_RDONLY, 0)) < 0) {
                fprintf(stderr, "%s: can't open( ) %s\n", prog, jname);
                cleanup(1);
            }
        }
        for (i = i0 = i1 = 0, dmax0 = dmax, xx = len0;; i++) {
            while (1) {
                for (j = dx[dmax].ijmp; j >= 0 && dx[dmax].jp.x[j] >= xx; j--)
                    ;
                                                                                                         ... readjmps
                if (j < 0 && dx[dmax].offset && fj) {
                    (void) lseek(fd, dx[dmax].offset, 0);
                    (void) read(fd, (char *)&dx[dmax].jp, sizeof(struct jmp));
                    (void) read(fd, (char *)&dx[dmax].offset, sizeof(dx[dmax].offset));
                    dx[dmax].ijmp = MAXJMP-1;           }
                else
                    break;          }
            if (i >= JMPS) {
                fprintf(stderr, "%s: too many gaps in alignment\n", prog);
                cleanup(1);
            }
            if (j >= 0) {
                siz = dx[dmax].jp.n[j];
                xx = dx[dmax].jp.x[j];
                dmax += siz;
                if (siz < 0) {              /* gap in second seq */
                    pp[1].n[i1] = -siz;
                    xx += siz;
                    /* id = xx - yy + len1 - 1                            */
                    pp[1].x[i1] = xx - dmax + len1 - 1;
                    gapy++;
                    ngapy -= siz;
/* ignore MAXGAP when doing endgaps */
                    siz = (-siz < MAXGAP || endgaps)? -siz : MAXGAP;
                    i1++;
                }
                else if (siz > 0) {        /* gap in first seq */
                    pp[0].n[i0] = siz;
                    pp[0].x[i0] = xx;
                    gapx++;
                    ngapx += siz;
/* ignore MAXGAP when doing endgaps */
                    siz = (siz < MAXGAP || endgaps)? siz : MAXGAP;
                    i0++;
                }
            }
```

TABLE 1-continued

```
        else
            break;
    }
    /* reverse the order of jmps */
    for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
    }
    for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
    }
    if (fd >= 0)
        (void) close(fd);
    if (fj) {
        (void) unlink(jname);
        fj = 0;
        offset = 0;
    }                                }
/*
* write a filled jmp struct offset of the prev one (if any): nw( )
*/
writejmps(ix)                                                                          writejmps
    int        ix;
{
    char       *mktemp( );
    if (!fj) {
        if (mktemp(jname) < 0) {
            fprintf(stderr, "%s: can't mktemp( ) %s\n", prog, jname);
            cleanup(1);
        }
        if ((fj = fopen(jname, "w")) = 0) {
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

| | | |
|---|---|---|
| ML-IAP chimera | XXXXXXXXXXXXXXX | (Length = 15 amino acids) |
| Comparison Protein | XXXXXYYYYYYY | (Length = 12 amino acids) |

% amino acid sequence identity =
(the number of identically matching amino acid residues between the two polypeptide sequences as determined by ALIGN-2) divided by (the total number of amino acid residues of the ML-IAP chimera polypeptide) =
5 divided by 15 = 33.3%

TABLE 3

| | | |
|---|---|---|
| ML-IAP chimera | XXXXXXXXXX | (Length = 10 amino acids) |
| Comparison Protein | XXXXXYYYYYYZZYZ | (Length = 15 amino acids) |

% amino acid sequence identity =
(the number of identically matching amino acid residues between the two polypeptide sequences as determined by ALIGN-2) divided by (the total number of amino acid residues of the ML-IAP chimera polypeptide) =
5 divided by 10 = 50%

TABLE 4

| | | |
|---|---|---|
| ML-IAP chimera | NNNNNNNNNNNNNN | (Length = 14 nucleotides) |
| Comparison DNA | NNNNNNLLLLLLLLLL | (Length = 16 nucleotides) |

% nucleic acid sequence identity =

TABLE 4-continued (the number of identically matching nucleotides between the two nucleic acid sequences as determined by ALIGN-2) divided by (the total number of nucleotides of the ML-IAP chimera nucleic acid sequence) =
6 divided by 14 = 42.9%

TABLE 5

| | | |
|---|---|---|
| ML-IAP chimera | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the ML-IAP chimera nucleic acid sequence) = 4 divided by 12 = 33.3%

Compositions and Methods of the Invention

ML-IAP Chimera Antibodies

In one embodiment, the present invention provides anti-ML-IAP chimera antibodies which may find use herein as therapeutic and/or diagnostic agents. Exemplary antibodies include polyclonal, monoclonal, humanized, bispecific, and heteroconjugate antibodies.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59–103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8–653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59–103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Plückthun, *Immunol. Revs.* 130:151–188(1992).

In a further embodiment, monoclonal antibodies or antibody fragments can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222: 581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et al., *Nuc. Acids. Res.* 21:2265–2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Human and Humanized Antibodies

The anti-MLIAP chimera antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-ML-IAP chimera antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggemann et al., *Year in Immuno*. 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552–553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564–571 (1993). Several sources of V-gene segments can be used for phage display. Clackson et al., *Nature*, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581–597 (1991), or Griffith et al., *EMBO J.* 12:725–734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163–167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of a ML-IAP chimera polypeptide as described herein. Other such antibodies may combine a ML-IAP chimera binding site with a binding site for another protein. Alternatively, an anti-ML-IAP chimera arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRM (CD16), so as to focus and localize cellular defense mechanisms to the ML-IAP chimera-expressing cell. Bispecific antibodies may also be used to localize cytotoxic agents to cells which express ML-IAP chimera. These antibodies possess a ML-IAP chimera-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps is rather cumbersome, and the product yields are low. Similar procedures are disclosed in WO 93/08829, and in Traunecker et al., *EMBO J.* 10:3655–3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH—CH1-flexible linker-VH—CH1-Fc region chain; or VH—CH1-VH—CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al., *Cancer Research* 53:2560–2565 (1993). Alternatively, an antibody can be engineered which has dual Fc regions and may thereby have enhanced complement lysis and ADCC capabilities. See Stevenson et al., *Anti-Cancer Drug Design* 3:219–230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Immunoconjugates

The invention also pertains to immunoconjugates comprising an antibody conjugated to a cytotoxic agent such as a chemotherapeutic agent, a growth inhibitory agent, a toxin (e.g. an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

In one preferred embodiment, an anti-ML-IAP chimera antibody (full length or fragments) of the invention is conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618–8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127–131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-ML-IAP Chimera Polypeptide Antibody-Maytansinoid Conjugates (Immunoconjugates)

Anti-ML-IAP chimera antibody-maytansinoid conjugates are prepared by chemically linking an anti-IAP chimera antibody to a maytansinoid molecule without significantly diminishing the biological activity of either the antibody or the maytansinoid molecule. An average of 3–4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research*

52:127–131 (1992). The linking groups include disufide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of inidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723–737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-ML-IAP chimera antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336–3342 (1993), Lode et al., *Cancer Research* 58:2925–2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Cytotoxic Agents

Other antitumor agents that can be conjugated to an IAP inhibitor include; adriamycin (doxorubicin), 4-tertiary butylphenol etoposide, taxol, camptothecin, methotrexate, vincristine or tamoxifen, BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

For selective destruction of the tumor, the IAP inhibitor may comprise a highly radioactive atom. A variety of radioactive isotopes are available for the production of radioconjugated proteins. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the IAP inhibitor may be biosynthesized or may be synthesized by chemical amino acid synthesis using suitable amino acid precursors involving, for example, fluorine-19 in place of hydrogen. Labels such as $Tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al., (1978) Biochem. Biophys. Res. Commun. 80: 49–57) can be used to incorporate iodine-123. "Monoclonal Antibodies in Immunoscintigraphy" (Chatal, CRC Press 1989) describes other methods in detail.

Conjugates of the IAP inhibitor and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the IAP inhibitor. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127–131 (1992); U.S. Pat. No. 5,208,020) may be used.

Alternatively, a fusion protein comprising the IAP inhibitor and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the IAP inhibitor may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Oligopeptides

IAP inhibitors may be oligopeptides that bind, preferably specifically, to an IAP polypeptide as described herein. IAP inhibitors may be chemically synthesized using known oligopeptide synthesis methodology or may be prepared and purified using recombinant technology. IAP inhibitors are usually at least about 3 amino acids in length, alternatively at least about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an IAP polypeptide as described herein. IAP inhibitors may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998–4002 (1984); Geysen et al., Proc. Natl. Acad. Sci. U.S.A., 82:178–182 (1985); Geysen et al., in Synthetic Peptides as Antigens, 130–149 (1986); Geysen et al., J. Immunol. Meth., 102:259–274 (1987); Schoofs et al., J. Immunol., 140:611–616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571, 689, and 5,663,143.

Although most phage display methods have used filamentous phage, lambdoid phage display systems (WO 95/34683; U.S. Pat. No. 5,627,024), T4 phage display systems (Ren, Z-J. et al. (1998) Gene 215:439; Zhu, Z. (1997) CAN 33:534; Jiang, J. et al. (1997) can 128:44380; Ren, Z-J. et al. (1997) CAN 127:215644; Ren, Z-J. (1996) Protein Sci. 5:1833; Efimov, V. P. et al. (1995) Virus Genes 10:173) and T7 phage display systems (Smith, G. P. and Scott, J. K. (1993) Methods in Enzymology, 217, 228–257; U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al., (1998) Mol Biotech. 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432, 018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

IAP inhibitors as described herein fused with another polypeptide sequence to generate a chimeric IAP inhibitor are also contemplated. Research on *Drosophila* protein ANTENNAPEDIA, discovered that 16 amino acids of the $3^{rd}$ helical domain could translocate across the cell membrane and enter into the cytoplasm intact (Prochiantz A., (1996) Curr. Opinion Neurobiol. (5):629–34, Derossi et al., (1998) Trends Cell Biol. (8) 84–87). This peptide was given the designation Penetratin (RQIKIWFQNRRMKWKK-NH2 (SEQ ID NO:7)). The mechanism by which the membrane translocation occurs is not yet defined, but recovery of the ANTENNAPEDIA peptide from the cytoplasm without degradation, and its low cell toxicity suggested that it could be fused to other peptide sequences to create chimeric molecules that could contact cells and be easily internalized with no loss of activity. The advantages of such a chimeric molecule are that no chemical coupling reaction is necessary, and the chimera can be either synthesized directly or inserted into a plasmid expression vector. Further advantages are that the Penetratin sequence can be fused with modified, for example biotinylated or phosphorylated, oligopeptides. An epitope tag sequence can be further added to facilitate recovery of the chimeric molecule with an antibody. Penetratin/Smac fusions have been designed and shown to successfully interact with IAPs (Arnt et al., (2002) Jour. Bio. Chem. 277 (46) 44236–44243). Arnt et al., fused 4–8 amino acids of Smac to the Penetratin sequence, and included a biotynlated version. After a 30 minute incubation, the Smac/Penetratin fusion polypeptide was recovered by streptavidin-agarose, the bound molecules were separated by SDS-PAGE and analyzed by immunoblotting. This experiment showed that the Smac/Penetratin fusion oligopeptide bound to XIAP and cIAPI in both cell lines tested. This group further demonstrated that the Smac/Penetratin fusion oligopeptide was active as it was an effective inhibitor of IAPs, as caspase activity was increased. While the Penetratin molecule is specifically described here, other oligopeptides that have been demonstrated to be internalized, such as TAT transcription factor, Herpes VP22, FGF-2 and lactoferrin are also contemplated.

Small Organic Molecules

IAP inhibitors that are organic molecules other than oligopeptides as defined herein that bind, preferably specifically, to an ML-IAP chimera polypeptide as described herein. IAP inhibitor small organic molecules may be identified and chemically synthesized using known methodology (see, e.g., PCT Publication Nos. WO00/00823 and WO00/39585). IAP inhibitors that are organic molecules are usually less than about 2000 Daltons in size, alternatively less than about 1500, 750, 500, 250 or 200 Daltons in size, wherein such organic molecules that are capable of binding, preferably specifically, to a IAP polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). IAP inhibitors may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

Screening for IAP Inhibitors With the Desired Properties

Techniques for generating oligopeptides and organic molecules that bind to IAP polypeptides have been described above. One may further select antibodies, oligopeptides or other organic molecules with certain biological characteristics, as desired.

The growth inhibitory effects of a IAP inhibitor may be assessed by methods known in the art, e.g., using cells which express an IAP polypeptide either endogenously or following transfection with the IAP gene. Preferably, this transfection is done with a ML-IAP chimera. For example, appropriate tumor cell lines and IAP-transfected cells may be treated with an IAP inhibitor at various concentrations for a few days (e.g., 2–7) days and stained with crystal violet or MTT or analyzed by some other colorimetric assay. Another method of measuring proliferation would be by comparing $^3$H-thymidine uptake by the cells treated in the presence or absence an IAP inhibitor. After treatment, the cells are harvested and the amount of radioactivity incorporated into the DNA quantitated in a scintillation counter. Appropriate positive controls include treatment of a selected cell line with a growth inhibitory antibody, oligopeptide or small organic molecule known to inhibit growth of that cell line. Growth inhibition of tumor cells in vivo can be determined in various ways known in the art. Preferably, the tumor cell is one that overexpresses an IAP polypeptide. Preferably, the IAP inhibitor will cause apoptosis of a IAP polypeptide expressing tumor cell in vitro or in vivo by about 25–100% compared to the untreated tumor cell, more preferably, by about 30–100%, and even more preferably by about 50–100% or 70–100%.

To select for an IAP inhibitor molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. IAP polypeptide-expressing tumor cells are incubated with medium alone or medium containing the appropriate IAP inhibitor. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those IAP inhibitors that induce statistically significant levels of cell death as determined by PI uptake may be selected as cell death-inducing IAP inhibitors.

To screen for IAP inhibitors which bind to a BIR domain on a IAP polypeptide of interest, polarization instrumentation such as an Analyst™ HT 96-384 (Molecular Devices Corp.) can be used. Samples for fluorescence polarization affinity measurements may be prepared in polarization buffer such as 50 mM Tris [pH 7.2], 120 mM NaCl, 1% bovine globulins and 0.05% octylglucoside) with 5-carboxyflourescein-conjugated peptides at 3–5 nM final concentrations. After an incubation step the reactions can be determined with standard cut-off filters for the fluorescein fluorophore (lex=485 nm; lem=530 nm) in 96-well black HE96 plates (Molecular Devices Corp.). The apparent Kd values can be determined from the EC50 values. The inhibition constants (Ki) can be determined as described previously (Keating et al., (2000) Proceedings of SPIE: In vitro diagnostic instrumentation Cohn, G. E., Ed. p 128–137).

Immunoliposomes

The anti-MLIAP chimera antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544, 545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286–288 (1982) via a disulfide interchange reaction. A chemotherapeutic agent is optionally contained within the liposome. See Gabizon et al., *J. National Cancer Inst.* 81(19):1484 (1989).

To screen for antibodies, oligopeptides or other organic molecules which bind to an epitope on a ML-IAP chimera polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-ML-IAP chimera antibody. Alternatively, or additionally, epitope mapping can be performed by methods known in the art. For example, the antibody sequence can be mutagenized such as by alanine scanning, to identify contact residues. The mutant antibody is initailly tested for binding with polyclonal antibody to ensure proper folding. In a different method, peptides corresponding to different regions of a ML-IAP chimera polypeptide can be used in competition assays with the test antibodies or with a test antibody and an antibody with a characterized or known epitope.

Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457–458 (1987)). Antibody-abzyme conjugates can be prepared as described herein for delivery of the abzyme to a tumor cell population.

The enzymes of this invention can be covalendy bound to the anti-ML-IAP chimera antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604–608 (1984).

ML-IAP Chimera Polypeptides

The present invention also provides newly identified and isolated nucleotide sequences encoding polypeptides referred to in the present application as ML-IAP chimera polypeptides. In particular, cDNAs (partial and full-length) encoding various ML-IAP chimera polypeptides have been identified and isolated, as disclosed in further detail in the Examples below.

The actual nucleotide sequences of those clones can readily be determined by the skilled artisan by sequencing of the deposited clone using routine methods in the art. The predicted amino acid sequence can be determined from the nucleotide sequence using routine skill.

Anti-ML-IAP Chimera Antibody and ML-IAP Chimera Polypeptide Variants

In addition to the anti-ML-IAP chimera antibodies and ML-IAP chimera polypeptides described herein, it is contemplated that anti-ML-IAP chimera antibody and ML-IAP chimera polypeptide variants can be prepared. Anti-ML-IAP chimera antibody and ML-IAP chimera polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-ML-IAP chimera antibody or ML-IAP chimera polypeptide, such as changing the number or position of glycosylation sites or altering the membrane anchoring characteristics.

Variations in the anti-MLIAP chimera antibodies and ML-AP chimera polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-ML-IAP chimera antibody or ML-IAP chimera polypeptide. Guidance in determining which amino acid residue may be inserted, substituted or deleted without adversely affecting the desired activity may be found by comparing the sequence of the anti-MIAP chimera antibody or ML-IAP chimera polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-ML-IAP chimera antibody and MLIAP chimera polypeptide fragments are provided herein. Such fragments may be truncated at the N-terminus or C-terminus, or may lack internal residues, for example, when compared with a full length native antibody or protein. Specifically these residues may comprise a substituted BIR domain as described herein. Certain fragments lack amino acid residues that are not essential for a desired biological activity of the anti-ML-IAP chimera antibody or ML-IAP chimera polypeptide.

Anti-ML-IAP chimera antibody and ML-IAP chimera polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired temini of the DNA fragment are employed at the 5' and 3' primers in the PCR. Preferably, anti-ML-IAP chimera antibody and ML-IAP chimera polypeptide fragments share at least one biological and/or immunological activity with a native anti-IAP antibody or IAP polypeptide.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function of ML-IAP chimera polypeptides are accomplished by selecting substitutions that differ significantly in their effect on maintaining (a) the structure of the ML-IAP chimera's backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the ML-IAP chimera variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081–1085 (1989)]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of variant, an isosteric amino acid can be used.

Any cysteine residue not involved in maintaining the proper conformation of the ML-IAP chimera also may be substituted, generally with serine, to improve the oxidative stability of the molecule and prevent aberrant crosslinking. Conversely, cysteine bond(s) may be added to the ML-IAP chimera to improve its stability A particularly preferred type of substitutional variant involves substituting one or more residues of a parent ML-IAP chimera. Generally, the resulting variant(s) selected for further development will have improved biological properties relative to the parent ML-IAP chimera from which they are generated. A convenient way for generating such substitutional variants involves affinity maturation using phage display. Briefly, a ML-IAP chimera contact site is mutated to generate amino substitutions at the site. The ML-IAP chimera variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate region sites for modification, alanine scanning mutagenesis can be performed to identify hypervariable region residues contributing significantly to ML-IAP chimera binding. Additionally, it is beneficial to analyze a crystal structure of the ML-IAP chimera/IAP inhibitor complex to identify contact points between the IAP inhibitor and the MLIAP chimera BIR domain. Such contact residues and neighboring residues are candidates for substitution according to the techniques elaborated herein. Once such variants are generated, the panel of variants is subjected to screening as described herein and ML-IAP chimeras with superior properties in one or more relevant assays may be selected for further development.

Selection and Transformation of Host Cells

Host cells are transfected or transformed with expression or cloning vectors described herein for ML-IAP chimera polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E5 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

ML-IAP chimeras can be produced in bacteria, in particular when glycosylation is not needed. Production in *E. coli* is faster and more cost efficient. For expression of proteins in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regions (TIR) and signal sequences for optimizing expression and secretion, these patents incorporated herein by reference. After expression, the ML-IAP chimera is isolated from the *E. coli* cell paste in a soluble fraction and can be purified.

In addition to prokaryotes, eukaryotic microbes such as filamentous fungi or yeast are suitable cloning or expression hosts for MIAP chimera encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968–975 (1991)) such as, e.g., *K. lactis* (MW98-8C, CBS683, CBS4574; Louvencourt et al., *J. Bacteriol.*, 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265–278 [1988]); *Candida; Trichoderma reesia* (EP 244,234); *Neurospora crassa* (Case et al., *Proc. Natl. Acad. Sci. USA*, 76:5259–5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284–289 [1983]; Tilburn et al., *Gene*, 26:205–221 [1983]; Yelton et al., *Proc. Natl. Acad. Sci. USA*, 81: 1470–1474 [1984]) and *A. niger* (Kelly and Hynes, *EMBO J.*, 4:475–479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated ML-IAP chimeras are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Droso-*

*phila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma line (Hep G2).

Host cells are transformed with the above-described expression or cloning vectors for ML-IAP chimeras and cultured in conventional nutrient media modified as appropriate for inducing promoters, selecting transformants, or amplifying the genes encoding the desired sequences.

Selection and Use of a Replicable Vector

The nucleic acid (e.g., cDNA or genomic DNA) encoding ML-IAP chimeras may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The ML-IAP chimera may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the ML-IAP chimera encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/14646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenoviris, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the LIP inhibitor-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the ML-IAP chimera-encoding nucleic acid sequence to direct mRNA synthesis. Promoters recognized by a variety of potential host cells are well known. Promoters suitable for use with prokaryotic hosts include the β-lactamase and lactose promoter systems [Chang et al., (1978) *Nature*, 275:615; Goeddel et al., (1979) *Nature*, 281:544], alkaline phosphatase, a tryptophan (trp) promoter system [Goeddel, (1980) *Nucleic Acids Res.*, 8:4057; EP 36,776], and hybrid promoters such as the tac promoter [deBoer et al., (1983) *Proc. Natl. Acad. Sci. USA*, 80:21–25]. Promoters for use in bacterial systems also will contain a Shine-Dalgarno (S.D.) sequence operably linked to the DNA encoding the ML-IAP chimera.

Examples of suitable promoting sequences for use with yeast hosts include the promoters for 3-phosphoglycerate kinase [Hitzeman et al., (1980) *J. Biol. Chem.*, 255:2073] or other glycolytic enzymes [Hess et al., (1968) *J. Adv. Enzyme Reg.*, 7:149; Holland, (1978) *Biochemistry*, 17:4900], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

ML-IAP chimera transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the ML-IAP chimera by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the ML-IAP chimera coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding ML-IAP chimeras.

Still other methods, vectors, and host cells suitable for adaptation to the synthesis of ML-IAP chimeras in recombinant vertebrate cell culture are described in Gething et al., *Nature*, 293:620–625 (1981); Mantei et al., *Nature*, 281:40–46 (1979); EP 117,060; and EP 117,058.

Culturing the Host Cells

The host cells used to produce the ML-IAP chimeras of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

This invention encompasses methods of screening compounds to identify those that prevent the effect of the ML-IAP chimera polypeptide (IAP inhibitors). Screening assays for antagonist drug candidates are designed to identify compounds that bind or complex with the ML-IAP chimera polypeptides. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with an ML-IAP chimera polypeptide under conditions and for a time sufficient to allow these two components to interact.

In binding assays, the interaction is binding and the complex formed can be isolated or detected in the reaction mixture. In a particular embodiment, the ML-IAP chimera polypeptide or the drug candidate is immobilized on a solid phase, e.g., on a microtiter plate, by covalent or non-covalent attachments. Non-covalent attachment generally is accomplished by coating the solid surface with a solution of the ML-IAP chimera polypeptide and drying. Alternatively, an immobilized antibody, e.g., a monoclonal antibody, specific for the ML-IAP chimera polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

To assay for antagonists, the ML-IAP chimera polypeptide may be added to a cell along with the compound to be screened for a particular activity and the ability of the compound to inhibit the activity of interest in the presence of the ML-IAP chimera polypeptide indicates that the compound is an antagonist to the ML-IAP chimera polypeptide. Alternatively, antagonists may be detected by combining the ML-IAP chimera polypeptide and a potential antagonist with ML-IAP chimera polypeptide under appropriate conditions for a competitive inhibition assay. The ML-IAP chimera polypeptide can be labeled, such as by radioactivity, such that the number of ML-IAP chimera polypeptide molecules bound to the competitor can be used to determine the effectiveness of the potential antagonist.

Potential antagonists include ML-IAP chimera inhibitors that bind to the BIR domain of the ML-IAP chimera polypeptide, thereby blocking the normal biological activity of the ML-IAP chimera polypeptide. Such peptides can be synthesized chemically and/or produced by recombinant DNA technology. See, e.g., Marasco et al., *Proc. Natl. Acad. Sci. USA* 90: 7889–7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturers instructions unless otherwise indicated. The source of those cells identified in the following examples, and throughout the specification, by ATCC accession numbers is the American Type Culture Collection, Manassas, Va.

Example 1

ML-IAP Chimera.

Previous structure and mutagenesis analysis of the XIAP-BIR3 domain revealed that the binding sites for Smac and caspase-9 are overlapping but not identical (Liu et al., (2000) Nature 408(6815): 1004–8.; Sun et al., (2000) J Biol Chem 275(43): 33777–81.; Wu et al., (2000) Nature 408 (6815): 1008–12.) For example, the three mutations W310A, E314S, and H343A were each shown to abolish inhibition of caspase-9 activity (Sun et al., (2000) J Biol Chem 275(43): 33777–81), suggesting that these residues may directly contact caspase-9, while only two of these three mutations (W310A and E314S) significantly reduced binding to a fluorescein-labeled Smac peptide (Liu et al., (2000) Nature 408(6815): 1004–8). Structural analysis of the XIAP-BIR3 domain in complex with Smac or a Smac-based peptide showed that XIAP residues Trp310 and Glu314 form part of the Smac-binding site, while His343 is located at the C-terminal end of the fifth α-helix and is remote from the Smac-binding site (Liu et al., (2000) Nature 408(6815): 1004–8; Wu et al., (2000) Nature 408(6815): 1008–12). Consistent with this, the H343A mutant binds the Smac-based peptide with wild-type affinity (Liu et al., (2000) Nature 408(6815): 1004–8).

The region of least sequence identity between ML-IAP-BIR and XIAP-BIR3 (for the structured portions of these BIR domains; residues Gly78-Ser171 for ML-IAP-BIR) corresponds to the C-terminal α-helix that includes His343 of XIAP (FIG. 3). In contrast, residues that define the Smac-peptide-binding site are highly conserved between the two BIR domains. Resolved at the level of their respective three-dimensional structure, ML-IAP-BIR and XIAP-BIR3 show that the structures, including the peptide-binding sites, are very similar (Franklin et al., (2003) Biochemistry 42: 8223–8231). In particular, the packing of helix-5 to the BIR domains is similar, despite the lack of sequence conservation. To ascertain if the ~300-fold lower potency for inhibition of caspase-9 activity by ML-IAP relative to XIAP (FIG. 4, Table 7) is due to residues in helix-5 that differ between the two proteins, a chimeric protein construct was made.

ML-IAP-BIR (amino acids 63–179 of accession number BIR7_HUMAN) was subcloned into a pET15b vector (Novagen™ for bacterial expression as described previously (Franklin et al., (2003) Biochemistry 42: 8223–8231). The subsequent vector, pet15bMLBIR, was then modified in a two step PCR based approach to generate MLXBIR3SG. First, amino acids 160–179 of ML-IAP-BIR were replaced with amino acids 336–348 of XIAP-BIR3 (accession number BIR4_HUMAN) to give pet15bMLXBIR3. Second, Ser 150 of ML-IAP-BIR was mutated to Gly to give pet15bMLXBIR3SG. The DNA sequence encoding MLXBIR3SG is given in FIG. 1 (SEQ ID NO:1). The translated amino acid sequence for MLXBIR3SG, with XIAP-BIR3 residues underlined is shown in FIG. 2 (SEQ ID NO:2).

The pet15bMLBIR vector was also modified to produce a C-terminally truncated version of ML-IAP-BIR that has the same number of amino acids as MLXBIR3 and MLXBIR3SG. An amino acid sequence alignment of the original ML-IAP-BIR construct (MLBIR), the C-terminally truncated variant of ML-IAP-BIR used in the present work (MLBIR-Q), the ML-IAP-BIR/XIAP-BIR3 chimera protein (MLXBIR3SG), and XIAP-BIR3, is given in FIG. 3. One liter cultures of *Escherichia coli* strain BL21 (DE3) transformed with pet15bMLXBIR3SG was induced with 1 mM IPTG for 4 hours at 30° C. in the presence of 50 μM zinc acetate. Cells were pelleted and resuspended in 50 ml/l Buffer A (50 mM Tris (pH 8.0), 300 mM NaCl, 5 mM β-mercaptoethanol, 0.5 mM PMSF, 2 mM benzamidine) with 5 mM imidazole. Cells were homogenized, microfluidized, and centrifuged. Lysate was passed over Ni-NTA agarose (Qiagen™) and eluted in Buffer A containing 300 mM imidazole. Finally, protein was passed over a Superdex™ 75 gel filtration (Pharmacia) column in buffer containing 50 mM Tris (pH 7.6), 200 mM NaCl, 5 mM DTT, 0.5 mM PMSF, 2 mM benzamidine, 50 mM zinc acetate. Protein was concentrated and stored at −80° C. Samples of MLBIR-Q and MLXBIR3 were prepared similarly. Proteins prepared in this manner were used in the crystallization and binding experiments.

Example 2

Production of Recombinant Proteins.

ΔCARD (caspase recruitment domain) human caspase 9 (lacking the first 138 residues) with Ala substitutions at residues 304 to 306 was produced as described previously (Boatright et al., (2003) Mol Cell 11: 529–541). The third BIR of MAP (residues 252–348) was also prepared as described previously (Sun et al., (2000) J Biol Chem 275 (43): 33777–81).

A PCR product containing amino acids 56–239 of Smac/DIABLO (accession number SMAC_HUMAN) was cloned into the XbaI/XhoI sites of a pet21b+ (Novagen) generating a C-terminal His$_6$ fusion. Pet21bSmac was transformed into *Escherichia coli* strain BL21(DE3) competent cells (Stratagene). Overnight cultures were diluted 1:100 and grown at 37° C. in LB media with 50 μg/ml carbenicillin to an A$_{600}$ of 0.8 with vigorous shaking. Isopropyl-β-D-1-thiogalacto-pyranoside (IPTG) was added to a final concentration of 1 mM and cultures were grown overnight at 16° C. Cell pellets were resuspended in Buffer A (50 mM Tris (pH 8.0), 300 mM NaCl, 0.5 mM PMSF, 2 mM benzamidine, 5 mM β-mercaptoethanol) with 5 mM imidazole and placed on ice for 30 minutes. Cells were homogenized, microfluidized, and centrifuged at 15,000 rpm for 45 minutes. Supernatant was loaded onto a Ni-NTA agarose column (Qiagen™), washed with 10 column volumes Buffer A with 10 mM imidazole, and eluted with 10 column volumes Buffer A with 300 mM imidazole. Fractions containing Smac protein were pooled, concentrated and loaded on a Superdex™ 200 sizing column. Protein eluted over one column volume into 50 mM Tris (pH 7.6), 300 mM NaCl, 0.5 mM PMSF, 2 mM benzamidine and 5 mM DTT. Fractions containing Smac protein were pooled and dialyzed against 3 changes of buffer containing 50 mM Tris (pH 7.6), 0.5 mM PMSF, 2 mM benzamidine and 5 mM DTT. The dialyzed sample was loaded onto a Q-Sepharose™ FF column (Pharmacia) and eluted over a 10 column volume gradient from zero to 1 M NaCl in buffer 50 mM Tris (pH 7.6), 0.5 mM PMSF, 2 mM benzamidine and 5 mM DTT. The cDNA encoding full-length ML-IAP plus a N-terminal $His_6$-tag was cloned into the pET15b(+) expression vector (Novagen). ML-IAP was expressed in E. coli strain BL21(DE3)pLysS. Expression of ML-IAP was induced with 0.5 mM IPTG at $A_{600}$=0.5 for 5 h. The protein was purified by affinity chromatography using chelating Sepharose™ (Pharmacia) charged with $NiSO_4$ according to the manufacturer's instructions. Eluted ML-IAP protein was >95% pure as judged by SDS-PAGE. The protein concentration of purified proteins was determined from the absorbance at 280 nm based on the molar absorption coefficients calculated from the Edelhoch relationship (Edelhoch, (1967) Biochemistry 6: 1948–1954).

Example 3

Caspase 9 Inhibition and Peptide Binding

The construct, MLXBIR3, is ~5-fold better at inhibiting caspase-9 than the wild-type ML-IAP-BIR construct of the same length, MLBIR-Q, but is still ~70-fold less potent at inhibiting caspase-9 than XIAP-BIR3. These data suggest that there are likely other important caspase-9 binding determinants in XIAP-BIR3, outside of the C-terminal helix-5, that are not present in ML-IAP. Polarization experiments were performed on an Analyst™ HT 96-384 (Molecular Devices Corp.). Samples for fluorescence polarization affinity measurements were prepared by addition of 1:2 serial dilutions starting at a final concentration of 5 µM of ML-IAP-BIR, MLBIR-Q, MLXBIR3, MLXBIR3SG, or 10 µM XIAP-BIR3 in polarization buffer (50 mM Tris (pH 7.2), 120 mM NaCl, 1% bovine globulins, 5 mM DTT, and 0.05% octylglucoside) to 5-carboxyflourescein-conjugated AVP-FAK(5-FAM)K (Hid-FAM) (SEQ ID NO: 3) at 5 nM final concentration. The reactions were read after an incubation time of 10 minutes at room temperature with standard cut-off filters for the fluorescein fluorophore ($\lambda_{ex}$=485 nm; $\lambda_{em}$=530 nm) in 96-well black HE96 plates (Molecular Devices Corp.). Fluorescence polarization values were plotted as a function of the protein concentration, and the $EC_{50}$ values were obtained by fitting the data to a 4-parameter equation using Kaleidagraph™ software (Synergy software, Reading, Pa.). The apparent $K_d$ values were determined from the $EC_{50}$ values.

Competition experiments were performed by addition of ML-IAP-BIR or BIR chimera constructs at 0.2 µM or XIAP-BIR3 protein at 0.5 nM to wells containing 5 nM of the HID-FAM probe as well as 1:3 serial dilutions of the Smac-9mer peptide (AVPIAQKSE) (SEQ ID NO:4) or wild-type mature Smac protein antagonists starting at a concentration of 300 µM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidagraph™ software (Synergy software; Reading, Pa.). Inhibition constants ($K_i$) for the antagonists were determined from the $IC_{50}$ values (Keating et al., (2000) *Putting the pieces together: contribution of fluorescence polarization assays to small-molecule lead optimization*. Proceedings of SPIE: In-Vitro Diagnostic Instrumentation.).

Determination of Caspase-9 Inhibitory Constants: Recombinant ΔCARD caspase 9 (300 nM final concentration in the assay) was preactivated in salt-free caspase buffer (20 mM PIPES, 10 mM EDTA, 0.1% CHAPS and 10% (w/v) sucrose, pH 7.2) for 15 min at 37° C. Following this, a range of inhibitor concentrations were preincubated with the enzyme for 20 min at 37° C. The assay was started by the addition of Ac-LEHD-AFC (100 µM final concentration) and measured kinetically for 30 min using an fmax Fluorescence Plate Reader (Molecular Devices) at an excitation wavelength of 405 nm and an emission wavelength of 510 nm. Reaction mixtures were thermostatically controlled at 37° C. The individual $K_i$ values for the inhibitors [I] were determined from the uninhibited substrate hydrolysis rate ($v_o$) and the inhibited rates ($v_i$), so that a plot of $(v_o/v_i)-1$ against [I] gives $K_i$(app), the equilibrium inhibition constant in the presence of substrate (Salvesen and Nagase, (1989) *Proteolytic enzymes: A practical approach*. R. J. Beynon and J. S. Bond. Oxford, IRL Press: 83–104).

The recent crystal structure of the complex between XIAP-BIR3 and caspase-9 (Shiozaki et al., (2003) Mol Cell 11: 519–527) revealed that in addition to residues from helix-5 and the peptide-binding site, residues from the C-terminal end of helix-3 and the immediately following loop in XIAP also contact caspase-9. Of the important contacts identified in this region of XIAP-BIR3, Gly326 is not conserved in ML-IAP (the corresponding residue is Ser 150). Mutation of this Gly residue to Glu in XIAP-BIR3 resulted in a loss of caspase-9 inhibition, presumably due to the introduction of a steric clash at the XIAP:caspase-9 interface (Shiozaki et al., (2003) Mol Cell 11: 519–527). To determine if the side chain of Ser 150 is interfering with the binding of MLXBIR3 to caspase-9, an additional construct in which this residue was substituted with a Gly residue as found in XIAP-BIR3 was made (FIG. 3). This construct, MLXBIR3SG, was found to inhibit caspase-9 with an apparent $K_i$ too low to measure accurately (<<1 nM), and is thus a more potent caspase-9 inhibitor than either XIAP-BIR3 ($K_i$(app)=13 nM) or ML-IAP ($K_i$(app)=3–5 µM) (FIG. 4, Table 7).

TABLE 7

Caspase-9 inhibition and peptide binding affinity of BIR domains

| Protein | Caspase-9 inhibition $K_i$(app) (nM) | Hid-FAM $K_d$ (µM) | Smac 9-mer $K_i$ (µM) | Smac $K_i$ (µM) |
|---|---|---|---|---|
| ML-IAP-BIR | 3,200[a] | 0.021 | 0.2 | 0.026 |
| MLBIR-Q | 4,600 | 0.020 | 0.35 | 0.054 |
| MLXBIR3 | 962 | 0.021 | ND | ND |
| MLXBIR3SG | <<1 | 0.030 | 0.34 | 0.059 |
| XIAP-BIR3 | 13 | 0.105 | 0.76 | 0.32 |

[a]$K_i$ for full-length ML-IAP

Example 4

Caspase-9 Binding.

Figure 5:
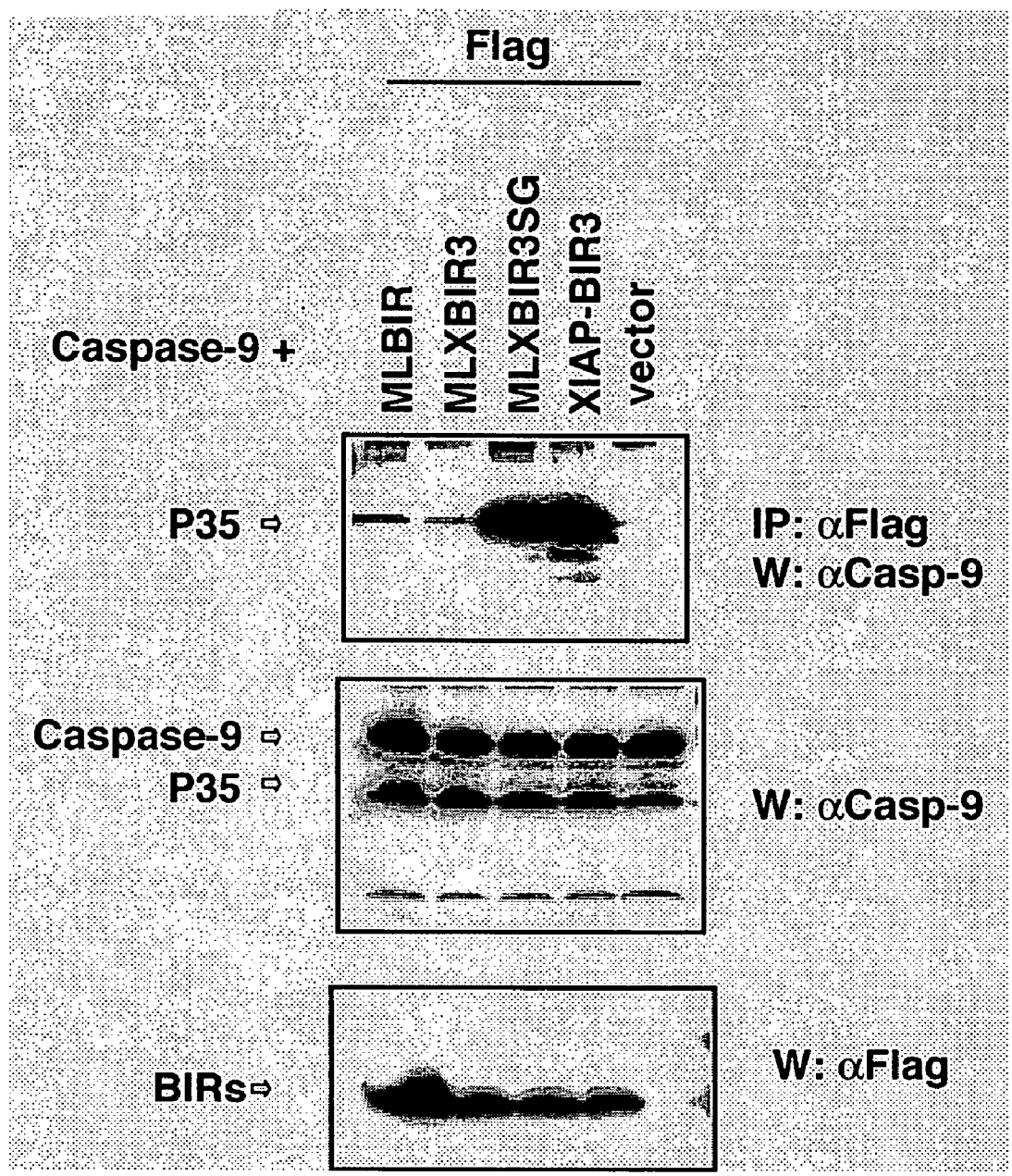
FIG. 5. Western blotting of immunoprecipitations of MLBIR, MLXBIR3, MLXBIR3SG as compared with XIAP-BIR3.

293T cells were transiently transfected with caspase-9 and Flag-tagged BIR domain proteins or vector. After 40 h, cells were lysed in NP40 lysis buffer (120 mM Tris, 150 mM NaCl, 1% NP-40, 1 mM DTT and protease inhibitor cocktail) and lysates immunoprecipitated (IP) with anti-Flag antibody. Samples were then Western blotted with anti-caspase-9 and anti-Flag antibodies. To better understand the mechanism by which the MLXBIR3 and MLXBIR3SG chimeric proteins inhibit caspase-9, binding to caspase-9 in cells was investigated. When overexpressed, caspase-9 undergoes autocatalytic processing and it is the processed form that physically interacts with XIAP and ML-IAP BIR domains. Accordingly, ML-IAP-BIR co-imnunoprecipitates processed caspase-9 but not its zymogen precursor. Western blotting revealed that MLXBIR3SG bearing the C-terminal portion of XIAP-BIR3 as well as the S150G mutation was significantly more efficient in binding caspase-9 than wild-type ML-IAP-BIR or MLXBIR3 that does not contain the S150G mutation (FIG. 5). Therefore, the caspase-9 binding efficiency of MLXBIR3SG appears to be similar to that of XIAP-BIR3 at this level of resolution.

Example 5

Inhibition of Apoptosis.

Figure 6:
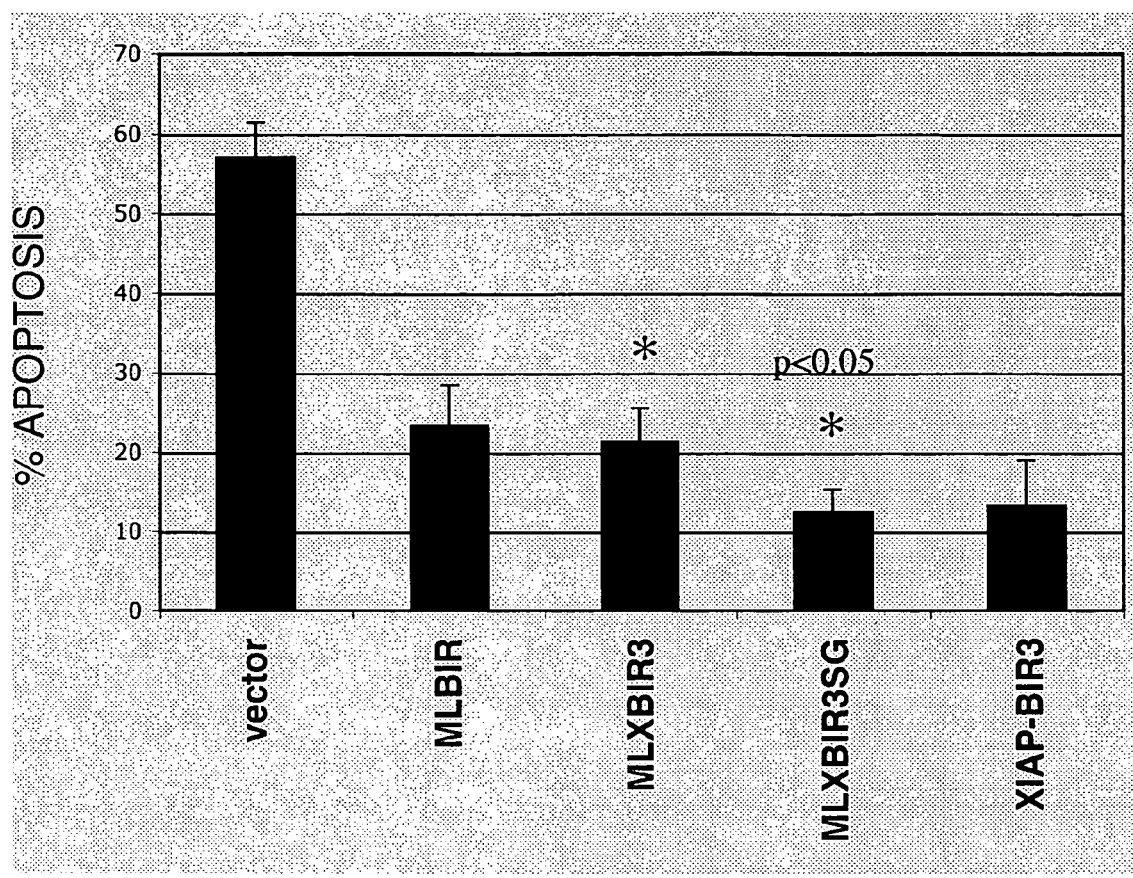
FIG. 6. Transfection with MLBIR, MLXBIR3, MLXBIR3SG or XIAP-BIR3 confers resistance to doxorubicin induced apoptosis.

MCF7 cells were transiently transfected with the reporter plasmid pCMV-βgal and either vector control alone or BIR domain constructs. Following transfection, cells were exposed to doxorubicin (adriamycin; 0.5 µg/ml), stained with X-gal and apoptosis assessed by counting live and dead transfected cells. Percentage apoptosis represents the mean value of at least four sample points and is representative of three independent experiments. To determine if the MLX-BIR3 and MLXBIR3SG chimeric proteins can block doxorubicin-induced apoptosis, the BIR domain proteins were transiently expressed in MCF-7 cells, and the cells were subsequently treated with doxorubicin. Analysis of apoptosis revealed that MLXBIR3SG was significantly more efficient in inhibiting doxorubicin-induced apoptosis than wild-type ML-IAP-BIR or MLXBIR3 that does not contain the S150G mutation (FIG. 6). The more efficient inhibition of apoptosis by MLXBIR3SG, relative to wild-type ML-IAP-BIR, is due to the improved binding and inhibition of caspase-9.

Example 6

Smac Binding.

MLXBIR3 and MLXBIR3SG chimeric proteins physically interact with mature Smac. 293T cells were transiently transfected with Flag-tagged Smac and Myc-tagged BIR domain proteins or vector control. After 40 h, cells were lysed in NP-40 lysis buffer (120 mM Tris, 150 mM NaCl, 1% NP40, 1 mM DTT and protease inhibitor cocktail) and lysates were immunoprecipitated (IP) with anti-Myc antibody. Samples were then Western blotted with anti-Flag and anti-Myc antibodies. FL-Smac designates full-length Smac protein.

Figure 7:
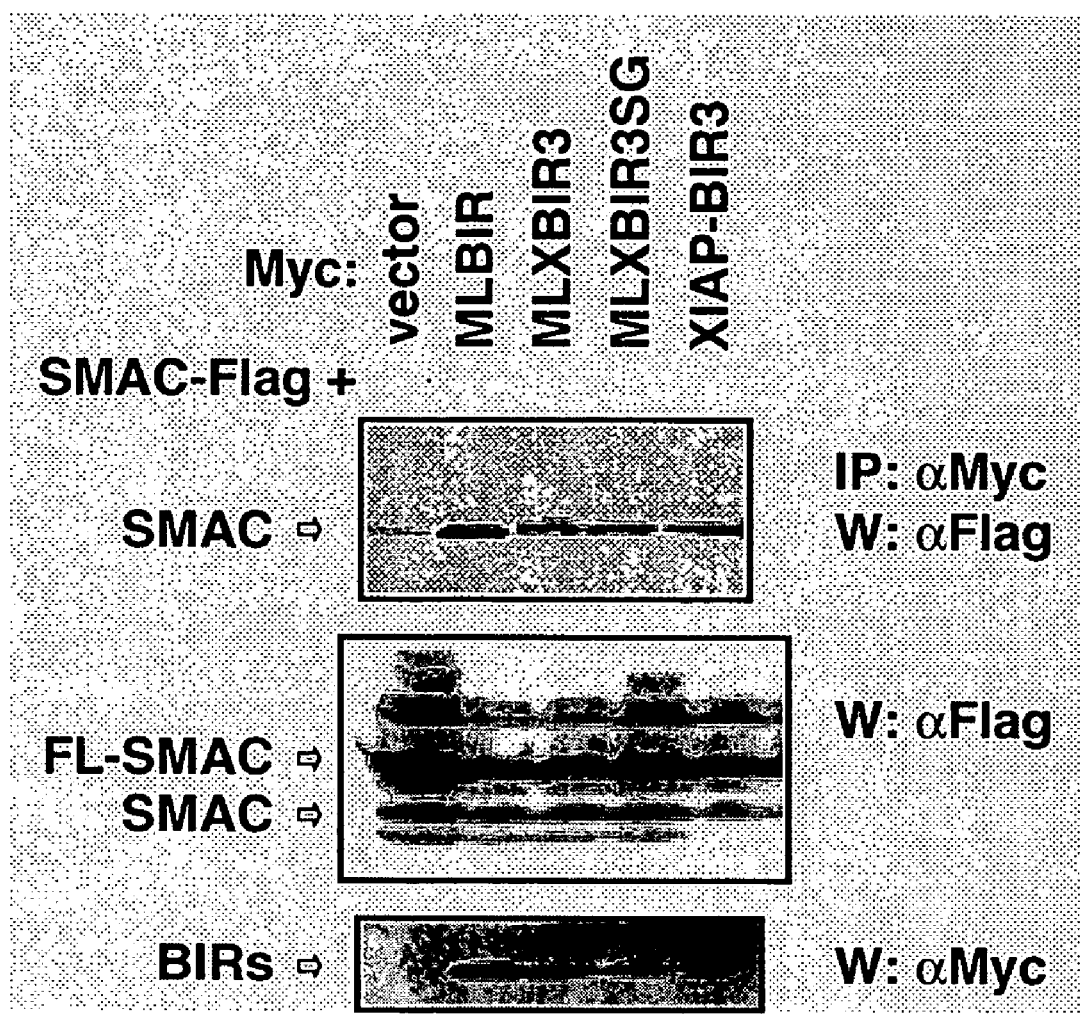
FIG. 7. Western blotting of immunoprecipitations of MLBIR, MLXBIR3 and MLXBIR3SG chimeric proteins as they physically interact with mature Smac as compared to XIAP-BIR3.

To examine the binding of Smac to the MLXBIR3 and MLXBIR3SG chimeric proteins, Smac was co-expressed with ML-IAP-BIR, MLXBIR3, MLXBIR3SG, XIAP-BIR3, or vector control. Upon overexpression, Smac was processed to its mature form in which the N-terminal 55 amino acids are cleaved (FIG. 7). Association of ML-IAP-BIR, XIAP-BIR3, and the MLXBIR3 and MLXBIR3SG chimeric proteins with mature Smac was demonstrated by immunoprecipitation and the interactions occurred with similar efficiency as shown in FIG. 7.

Example 7

Quantification of Smac Binding to BIR Domain.

Figure 8:
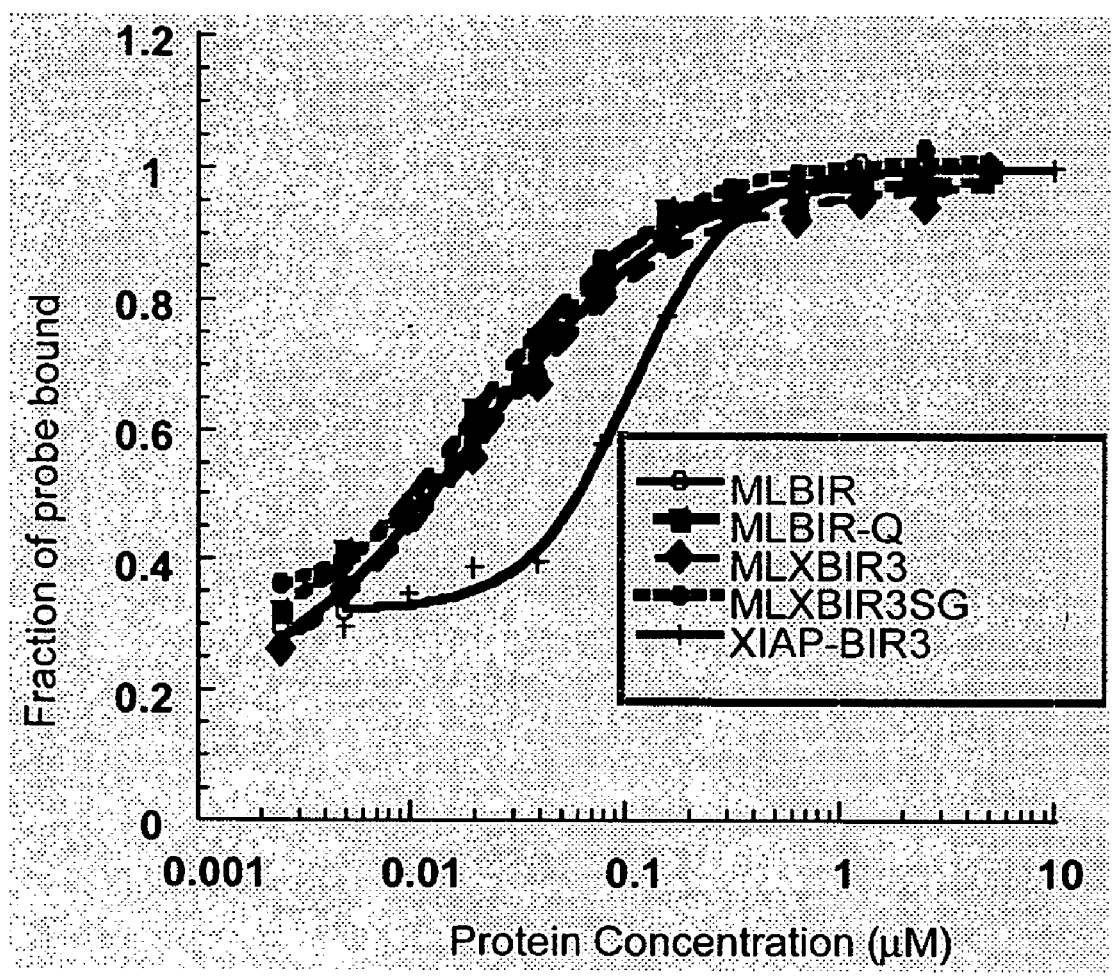
FIG. 8. Binding of 5-carboxyfluorescein-labeled Hid-based peptide (Hid-FAM) to BIR domains, MLBIR, MLBIR-Q, MLXBIR3, MLXBIR3SG, and XIAP-BIR3, as determined by a fluorescence polarization-based assay. $K_d$ values are listed in Table 7.
Figure 9:
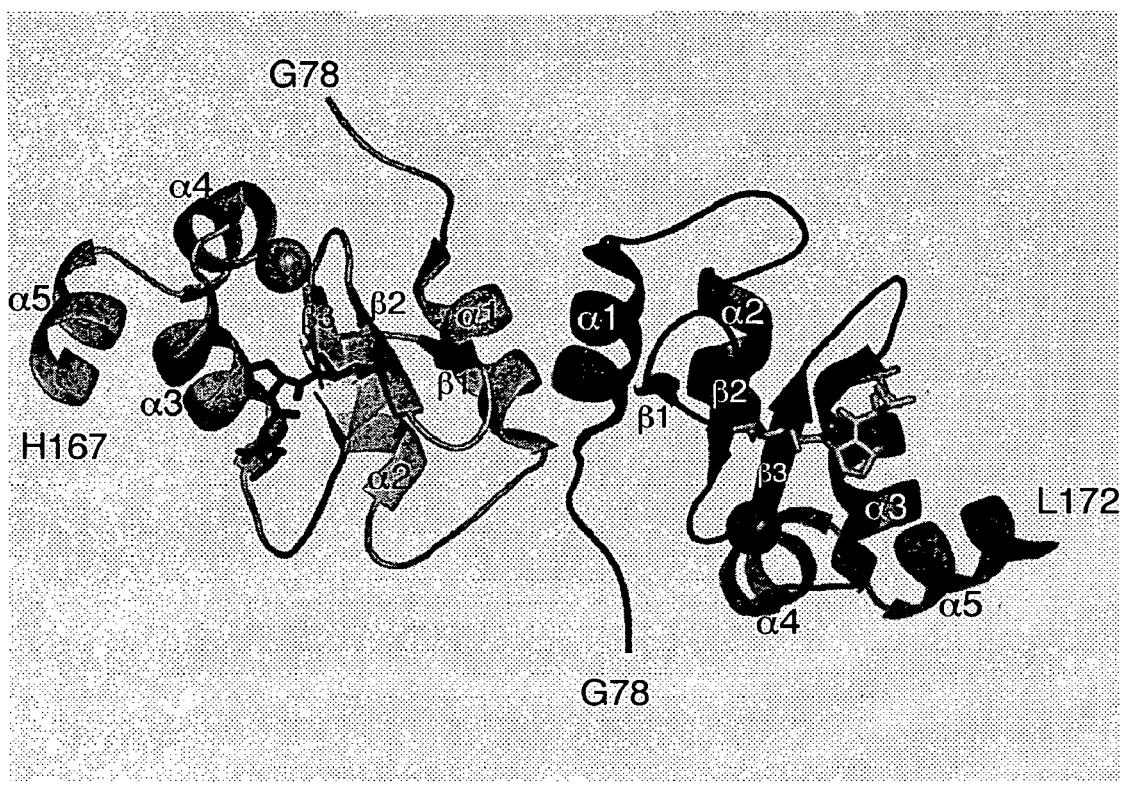
FIG. 9. The asymmetric unit of the MLXBIR3SG-AVPIAQKSE complex crystals. Both copies of the MLXBIR3SG protein are shown in a ribbon representation, and both copies of the ordered portion of the peptide in a stick representation. One complex (chains A and C) is on the left, with a light-colored protein and a dark peptide; the other complex (chains B and D) is on the right. The zinc atoms bound by the two MLXBIR3SG proteins are shown as spheres. The non-crystallographic 2-fold axis relating the two complexes is in the middle of the figure, roughly perpendicular to the plane of the page.

To quantify the binding of Smac to the BIR domains, the affinities of a peptide corresponding to the N-terminal nine residues of mature Smac (AVPIAQKSE) (SEQ ID NO: 4) and the mature Smac protein were determined using a fluorescence polarization-based competition assay as described in Example 3, with a Hid-based 5-carboxyfluorescein-labeled peptide (Hid-FAM) as the probe. The $K_d$ values of 5-carboxyfluorescein-labeled Hid-FAM binding to BIR domains, MLBIR, MLBIR-Q, MLXBIR3, MLXBIR3SG, and XIAP-BIR3, as determined by a fluorescence polarization-based assay are listed in Table 7. The binding affinity of the Hid-FAM probe for each of the BIR domains was determined directly using a fluorescence polarization-based assay and the result is shown graphically in FIG. 8. The $K_d$ values for the Hid-based peptide binding to the chimeric BIR domain constructs are similar to those determined for binding to the wild-type ML-IAP-BIR constructs (20–30 nM; Table 7), indicating that the chimeric substitutions have not perturbed the peptide-binding site of ML-IAP-BIR. Similarly, the $K_i$ values for MLXBIR3SG binding to the AVPIAQKSE (SEQ ID NO: 4) peptide or mature Smac are essentially identical to those determined for the wild-type ML-IAP-BIR construct of the same length (MLBIR-Q) and within the experimental uncertainty when compared to the slightly longer ML-IAP-BIR construct (MLBIR) (Table 7). These data suggest further that the Smac-binding site on the chimeric BIR domain is identical to that of wild-type ML-IAP-BIR. Therefore, the increased efficiency of inhibition of apoptosis observed for MLXBIR3SG relative to MLBIR can be attributed to its improved binding to and inhibition of caspase-9.

Example 9

Chimera/Complex Co-crystalization and Soaking.

To understand further the contributions to improved caspase-9 binding and inhibition of the ML-IAP and XIAP residues in the MLXBIR3SG BIR domain construct, the protein was crystallized in complex with Smac- or Hid-based peptides. Crystals of MLXBIR3SG complexed with the peptides AVPW (Hid) (SEQ ID NO:5) or AVPIAQKSE (SEQ ID NO: 4) (Smac) were removed from the crystallization drop and transferred to a stabilizer drop (typically 5 µl) containing 100 mM Bis-tris, pH 6; 200 mM lithium sulfate; 30% (w/v) polyethylene glycol 3350; and 0.5–1.0 mM of the compound to be soaked in. Compounds were reconstituted from lyophilized powder in either 10 mM MES, pH 5.5 or in neat DMSO. Compound stock solution concentrations were 30–50 mM and were verified by $A_{280}$ when possible. Crystals were generally left in the soaking solution overnight, as a hanging drop over a reservoir of the same solution to prevent evaporation; however, a 3-hour soak of compound Inhibitor 1 (Table 8) was also successful. Crystals were then transferred to a cryostabilizer containing 100 mM Bis-tris, pH 6; 200 mM lithium sulfate; 30% (w/v) polyethylene glycol 3350; 15% (v/v) ethylene glycol; and 0.5–1.0 mM of the same compound used in the soaking stage. After 15–20 minutes in the cryostabilizer, the crystals were frozen in liquid nitrogen. Crystals of the parent complexes (AVPW (SEQ ID NO:5) and AVPIAQKSE (SEQ ID NO: 4)) were prepared in the same manner, except that the appropriate peptide was substituted for the inhibitor compound in the soaking and cryostabilizer solutions.

Datasets for the various antagonist complexes were collected at the Stanford Synchrotron Radiation Laboratory, the Advanced Photon Source (Argonne, Ill.), and the Cornell High Energy Synchrotron Source. Data statistics are listed in Table 8. The first of these structures to be solved (Inhibitor 1) was solved by molecular replacement with the program AMoRe, using the previously determined structure of wild-type ML-IAP-BIR (chain E; PDB accession code 1OXN) as a search model. Initial refinement of the Inhibitor 1 complex structure involved replacing the wild-type ML-IAP residues in the model with their MLXBIR3SG counterparts, placing the antagonist into electron density in the peptide-binding site, and rebuilding protein side chains into electron density. Subsequent refinement involved cycles of positional, anisotropic B factor, and translation-libration-screw (TLS) refinement as implemented in the program Refmac5 (Murshudov et al., (1997) Acta Crystallogr D53: 240–255), automated water addition and removal using the program Arp/wArp (Perrakis et al., (2001) Acta Crystallogr D57 (Pt 10): 1445–50), and manual model adjustment using the program O (Jones et al., (1991) Acta Crystallogr A47: 110–9).

The Inhibitor 1 complex structure, refined to 1.8 Å, was used as the reference until data were collected to 1.3 Å on the Inhibitor 3 soak complex. The Inhibitor 3 structure was extensively refined by positional, anisotropic B factor, and TLS refinement using Refmac, with hydrogen atoms added in the riding positions. An ordered Bis-tris molecule, ethylene glycol molecule, and lithium ion were added to the model, along with a number of additional water molecules.

The Inhibitor 3 complex was used as the new reference for all other inhibitor structures. Refinement of these structures started with the Inhibitor 3 complex model, stripped of the antagonist molecule and all waters within 10 Å of it. After one round of refinement of the antagonist-free model, the new antagonist was built into difference electron density, new water molecules were automatically picked, and the entire new complex model subjected to several rounds of positional, anisotropic B factor, and TLS refinement. Refinement statistics for all complexes determined to date are summarized in Table 8.

Figure 11:
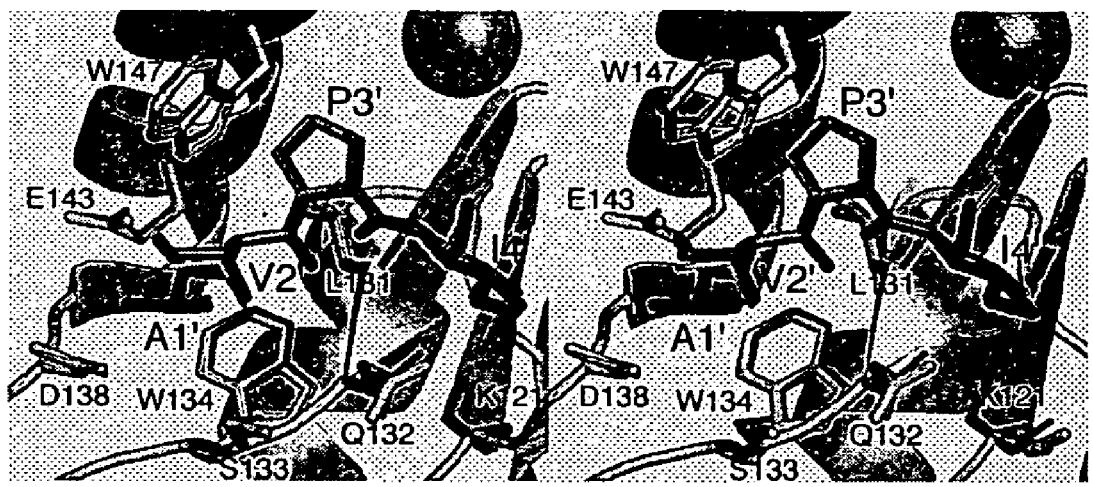
FIG. 11. A stereoview of the superposition of the peptide-binding sites of wild-type ML-IAP-BIR and the chimeric protein MLXBIR3SG. The backbone of the MLXBIR3SG chimera is shown in a ribbon representation. Side chains of MLXBIR3SG and wild-type ML-IAP-BIR that are within 3.8 Å of the peptide are shown in stick representation, as is the AVPI portion of the AVPIAQKSE peptide from both complexes. The MLXBIR3SG-AVPIAQKSE complex is colored like the left complex in FIG. 9: light gray protein side chains and black peptide. The wild-type ML-IAP-BIR complex is colored medium gray for both protein and peptide, and depicted with thinner sticks.

The MLXBIR3SG chimera complex crystals are in space-group $P4_12_12$, with unit cell dimensions approximately 87×87×74 Å, containing two copies of the protein-peptide complex in the crystallographic asymmetric unit as shown in FIG. 11. These two copies are very similar, with an all-atom RMSD of 1.4 Å excluding residues 100–101, which adopt different conformations in the two copies due to crystal packing. In both cases the peptide-binding site is exposed to bulk solvent, despite the two copies of the complex having different crystal packing environments; no significant crystal packing contacts are made by either the residues of the peptide-binding site or the bound peptide itself. In soaking experiments where the AVPW (SEQ ID NO:5) peptide is exchanged for another compound, both copies of the peptide are replaced with equal efficiency.

Figure 10:
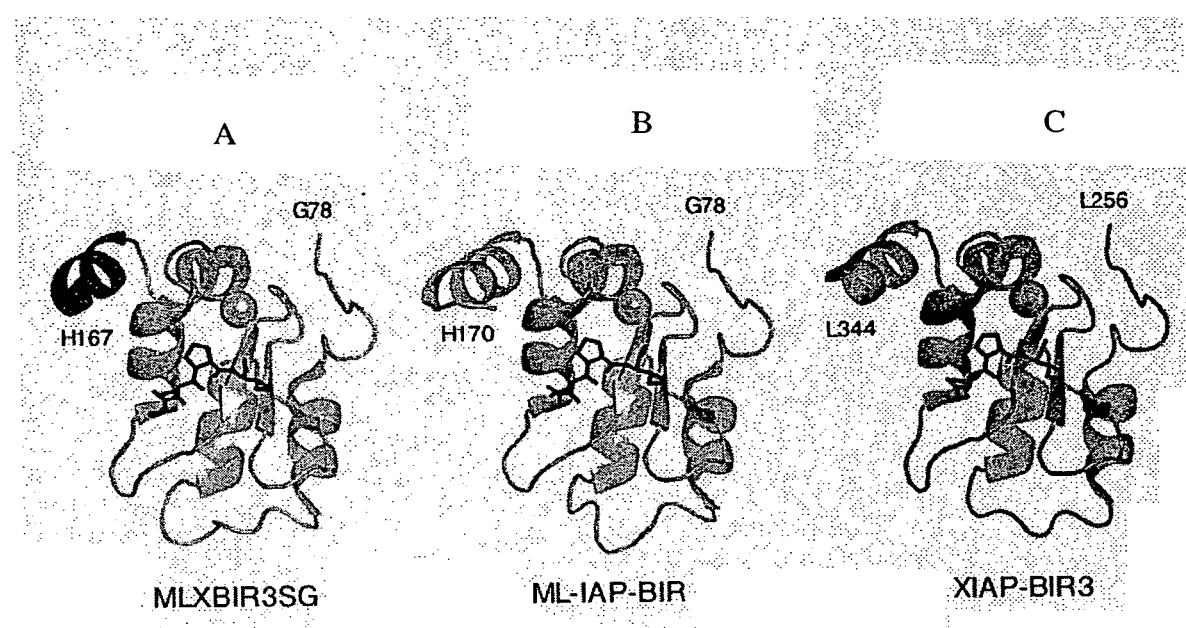
FIG. 10. A comparison of three BIR domain-peptide complexes. The MLXBIR3SG complex with the AVPIAQKSE peptide is shown in FIG. 10A, with the ordered chimeric portion (residues 150 and 160–167) in a darker color ribbon. The wildtype ML-IAP-BIR complex with an AVPIAQKSE peptide (chains. E and F from PDB accession code 1OXQ) is shown in the same orientation in FIG. 10B, while the equivalent complex for XIAP-BIR3 (residues 1–4 of chain B and all of chain C from PDB accession code 1G73) is shown in FIG. 10C.

The crystallized MLXBIR3SG construct contains 133 residues: a 23-residue $His_6$-tag with a thrombin cleavage site, followed by residues 63–172 of ML-IAP; residues 150 and 160–172 are replaced by their XIAP-BIR3 counterparts. The $His_6$-tag and residues 63–77 of ML-IAP are disordered in both copies of MLXBIR3SG in the asymmetric unit of the crystals. Residues 78–167 of copy A and 78–172 of copy B are well ordered, as are the bound antagonists, for which all atoms are clearly visible in electron density maps. All atoms of the AVPW (SEQ ID NO:5) peptide are also well ordered and visible in electron density maps; however, as observed for wild-type ML-IAP-BIR, only the first four residues (AVPI) of the Smac-based nine-residue peptide are well ordered. The structure of the MIXBIR3SG chimeric protein is essentially identical to that of wild-type ML-IAP-BIR (FIG. 10). The two structures can be superposed with an RMSD on C-alpha atoms of 1.1 Å on all residues (chain A of MLXBIR3SG versus chain E of wild-type ML-IAP-BIR), and 0.6 Å excluding residues 100–101. Helix 5 of MLXBIR3SG, which contains all of the chimeric substitutions except S150G, has not moved relative to the rest of the BIR domain even though nearly all of the residues on this helix are now different than those of wild-type ML-IAP-BIR. The peptide-binding region of ML-IAP-BIR is unaffected by the chimera substitutions (FIG. 11): no atom of the chimeric residues is closer than 10 Å to the bound peptide. As would be expected given the similarity of the peptide-binding site, the all-atom RMSD between the same peptide (AVPIAQKSE (SEQ ID NO: 4)) bound to the two different proteins is less than 0.2 Å.

Like wild-type ML-IAP-BIR, the MLXBIR3SG chimera closely resembles other BIR domains, in particular XIAP-BIR3 (FIG. 8), which can be superposed on MLXBIR3SG with a C-alpha RMSD of 0.5 Å (chain C of PDB code 1G73 versus chain A of the MLXBIR3SG structure, again excluding residues 100–101). The chimeric XIAP residues in MLXBIR3SG adopt the same side chain conformations as they do in XIAP-BIR3. Three residues in helix 5 make up the majority of the interface with the rest of the BIR domain; the MLXBIR3SG chimeric substitutions for these residues (F162Y, V1631, V1661) only add three heavy-atoms at the periphery of the interface, none of which affect packing of this helix. Thus, helix 5 of MLXBIR3SG looks like the corresponding helix of XIAP-BIR3, but packs with the rest of the domain exactly like the equivalent helix in wild-type ML-IAP-BIR.

TABLE 8

Data collection and refinement statistics.

| Antagonist | AVPW | AVPIAQKSE | Inhibitor 1 | Inhibitor 2 | Inhibitor 3 | Inhibitor 4 |
|---|---|---|---|---|---|---|
| Resolution (Å) | 50–1.6 | 50–1.7 | 50–1.8 | 40–2.5 | 50–1.3 | 20–1.8 |
| | (1.681.62) | (1.77–1.71) | (1.86–1.80) | (2.59–2.50) | (1.35–1.30) | (1.86–1.80) |
| Unique reflections | 32349 | 31742 | 24948 | 10335 | 69936 | 26912 |
| | (1397) | (2793) | (1570) | (983) | (6028) | (2612) |
| $R_{sym}$ | 0.068 | 0.115 | 0.107 | 0.163 | 0.042 | 0.053 |
| | (0.460) | (0.664) | (0.581) | (0.577) | (0.256) | (0.351) |

TABLE 8-continued

Data collection and refinement statistics.

| Antagonist | AVPW | AVPIAQKSE | Inhibitor 1 | Inhibitor 2 | Inhibitor 3 | Inhibitor 4 |
|---|---|---|---|---|---|---|
| $I/\sigma(I)$ | 20.9 (1.7) | 21.4 (2.2) | 14.3 (1.5) | 10.0 (2.5) | 41.9 (3.1) | 28.9 (6.7) |
| Redundancy | 5.8 (0.7) | 12.0 (7.2) | 5.4 (1.6) | 6.0 (5.1) | 5.2 (2.0) | 8.3 (6.7) |
| $R_{cryst}$ | 0.161 | 0.213 | 0.155 | 0.185 | 0.142 | 0.158 |
| $R_{free}$ | 0.180 | 0.250 | 0.175 | 0.236 | 0.151 | 0.180 |
| Bond RMSD (Å) | 0.009 | 0.011 | 0.009 | 0.006 | 0.012 | 0.008 |
| Angle RMSD (°) | 1.1 | 1.2 | 1.5 | 1.0 | 1.5 | 1.2 |

$$R_{sym} = \sum_{hkl} |I - \langle I \rangle| \Big/ \sum_{hkl} I$$

$$R_{cryst} = \sum_{hkl} ||F_{(obs)}| - |F_{(calc)}|| \Big/ \sum_{hkl} |F_{(obs)}|$$

$R_{free} = R_{cryst}$ for a random 5% of reflections (the same set is used for all structures)
Numbers in parentheses are for the highest resolution shell.

Example 12

TR-FRET Analysis of Competition Experiments.

Figure 12:
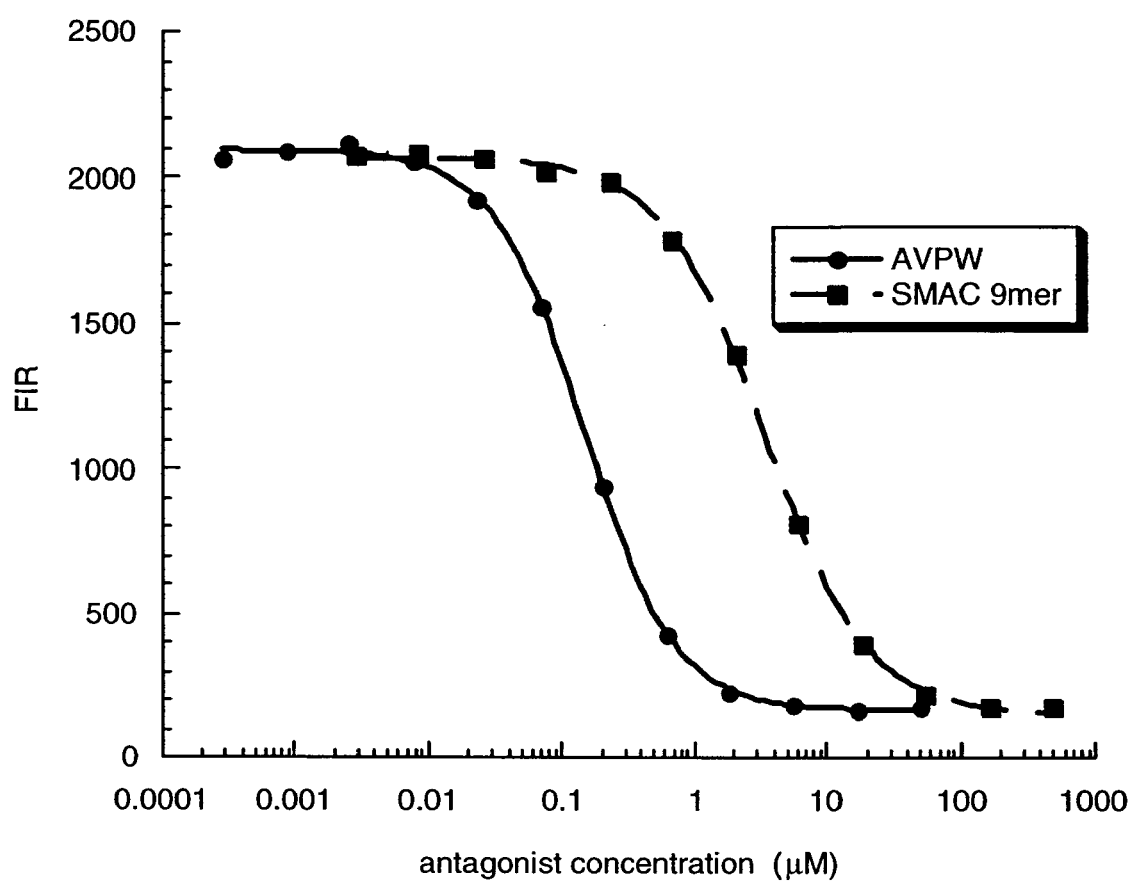
FIG. 12. Binding of AVPW and Smac 9-mer (AVPIAQKSE) peptides to MLXBIR3SG, as determined by Time-Resolved Fluorescence Resonance Energy Transfer (TR-FRET) competition assay. The $IC_{50}$ values determined from this experiment are 0.15 and 3.46 ρM for AVPW and AVPIAQKSE, respectively.

Time-Resolved Fluorescence Resonance Energy Transfer (TR-FRET) competition experiments (Kolb et al., (1996) J. Biomol. Screening 1 (4): 203–210) were performed on the Wallac Victor2 Multilabeled Counter Reader™ (Perkin Elmer Life and Analytical Sciences, Inc.). A reagent cocktail containing 300 nM $His_6$-tagged MLXBIR3SG, 200 nM biotinylated Smac peptide (AVPIAQK-biotin), 5 µg/ml anti-$His_6$ antibody-allophycocyanin (XL665) conjugate (CISBio. International), and 200 ng/ml europium-labeled streptavidin (Perkin Elmer) was prepared in reagent buffer (50 mM Tris (pH 7.2), 120 mM NaCl, 0.1% bovine globulins, 5 mM DTT and 0.05% octylglucoside). Alternatively, this cocktail can be made using optimized concentrations of europium-labeled anti-$His_6$ antibody (Perkin Elmer) instead of the anti-$His_6$ antibody-allophycocyanin conjugate, and streptavidin-allophycocyanin conjugate (Perkin Elmer) instead of europium-labeled streptavidin. The reagent cocktail was incubated at room temperature for 30 minutes. After incubation, the cocktail was added to 1:3 serial dilutions of an antagonist (i.e. AVPW at a starting concentration of 50 µM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and allophycocyanin (665 nm). Data are calculated as a ratio of the emission signal of allophycocyanin at 665 nm to the emission signal of europium at 615 nm (these ratios are multiplied by a factor of 10,000 for ease of data manipulation). The resulting values were plotted as a function of antagonist concentration and fit to a 4-parameter equation using Kaleidagraph™ software (Synergy Software, Reading, Pa.). Indications of antagonist potency were determined from the $IC_{50}$ values. Example plots showing the binding of AVPW and AVPIAQKSE (Smac 9-mer) antagonist peptides to MLXBIR3SG are given in FIG. 12. The TR-FRET assay may also be used as a high throughput screen, using biotinylated peptide libraries or small molecule libraries in place of the biotinylated Smac peptide as described above.

Example 13

Chimera for NMR

Nuclear magnetic resonance (NMR)-based methods might be used to identify compounds that bind to MLXBIR3SG, and to aid their development into potent antagonists that could be used as lead compounds in a drug discovery process. In particular, the SAR-by-NMR (structure-activity relationship by NMR) method, and variations thereof, have been widely applied to drug discovery by NMR [Shuker et al., (1996) Science 274, 1531–1534].

Such methods are based on the use of protein chemical-shift changes to identify low-affinity ligands that target relevant binding sites on the protein. A prerequisite of such chemical-shift mapping methods is reasonable resolution, and preferably sequence-specific assignments, of protein resonances in two-dimensional heteronuclear-correlation spectra (either $^{15}N$, $^1H$- or $^{13}C$,$^1H$-correlation spectra). Unfortunately, the MLXBIR3SG chimeric protein domain aggregates significantly in the concentration range required for NMR spectroscopy, resulting in poor quality NMR spectra that preclude the use of protein chemical-shift methods to identify ligands.

Figure 13:
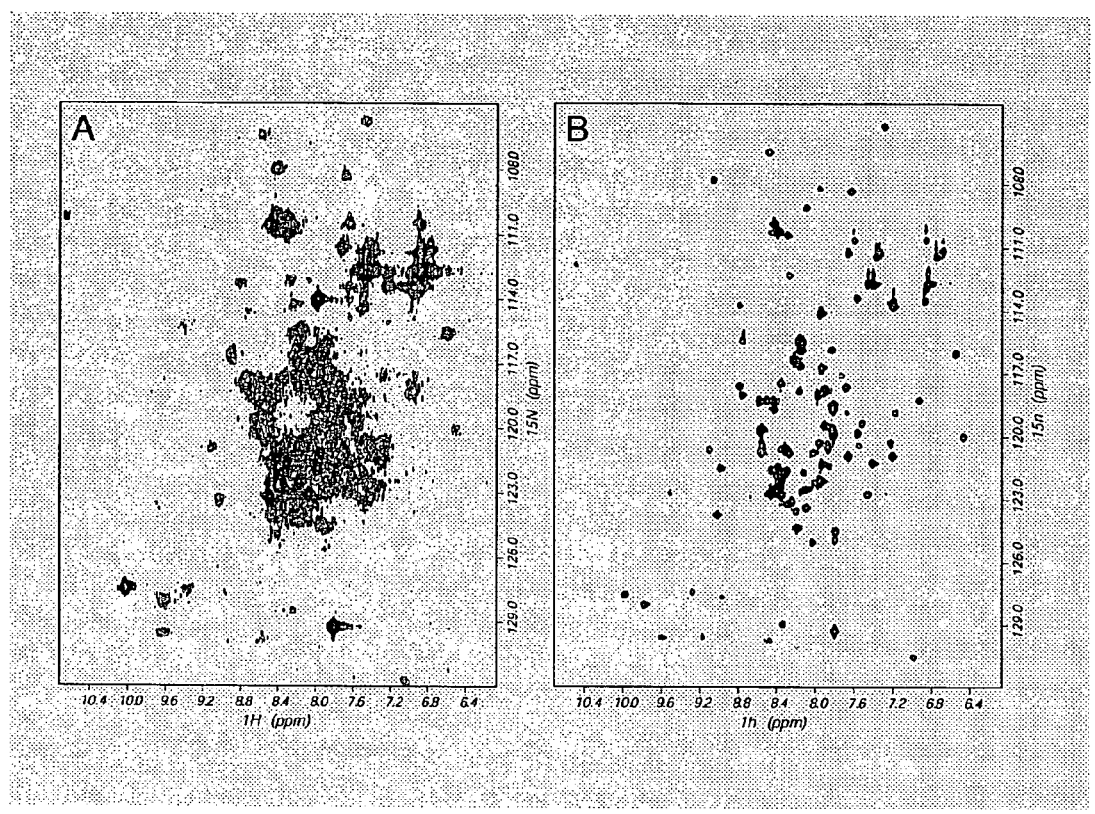
FIG. 13A–B. $^{15}N$,$^{1}H$-HSQC spectra of (A) 0.5 mM MLXBIR3SG in 50 mM potassium phosphate (pH 7.2), 150 mM sodium chloride, and (B) 0.1 mM Ala71Glu/Ala73Glu/Phe81Glu/Leu89Asp mutant MLXBIR3SG in 50 mM Bis-Tris propane (pH 7.0), acquired at 25° C. on Bruker DRX-500 and DRX-600 NMR spectrometers, respectively.

However, the introduction of specific amino-acid mutations within an interface identified previously from the X-ray crystal structure of ML-IAP-BIR [Franklin et al. (2003) Biochemistry 42, 8223–8231] can reduce the solution aggregation and consequently improve the quality of the NMR spectra of MLXBIR3SG. Introduction of the mutations Ala71Glu, Ala73Glu, Phe81Glu, and Leu89Asp, into the background of MLXBIR3SG results in a protein (FIG. 14, SEQ ID NO:6) that has dramatically improved spectral quality as shown in FIG. 13, and is thus amenable to NMR-based screening methods.

Example 14

Preparation of Antibodies

This example illustrates preparation of monoclonal antibodies which can specifically bind a ML-IAP chimera.

Techniques for producing the monoclonal antibodies are known in the art and are described, for instance, in Goding, supra. Immunogens that may be employed include purified ML-IAP chimera, fusion proteins containing a ML-IAP chimera, and cells expressing recombinant ML-IAP chimera on the cell surface. Selection of the immunogen can be made by the skilled artisan without undue experimentation.

Mice, such as Balb/c, are immunized with the ML-IAP chimera immunogen emulsified in complete Freund's adjuvant and injected subcutaneously or intraperitonealiy in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-ML-IAP chimera antibodies.

After a suitable antibody titer has been detected, the animals "positive" for antibodies can be injected with a final intravenous injection of ML-IAP chimera. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against ML-IAP chimera. Determination of "positive" hybridoma cells secreting the desired monoclonal antibodies against ML-IAP chimera is within the skill in the art.

The positive hybridoma cells can be injected intraperitoneally into syngeneic Balb/c mice to produce ascites containing the anti-ML-IAP chimera monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of screening for a compound that inhibits caspase interaction with a melanoma-inhibitor of apoptosis (ML-IAP) chimera comprising:
   a. contacting a caspase polypeptide and an IAP polypeptide in the presence of said compound, wherein said IAP polypeptide is SEQ ID No: 2;
   b. detecting the amount of caspase activity when compared to the amount of caspase activity without the presence of the modulating compound.

2. The method of claim 1, wherein said caspase is selected from the group consisting of caspase 3, and caspase 9.

3. The method of claim 1, wherein caspase activity is detected using an antibody.

4. The method of claim 1, wherein caspase activity is detected by cleavage of a protein substrate.

* * * * *

UNITED STATES PATENT AND TRADEMARK OFFICE
CERTIFICATE OF CORRECTION

PATENT NO. : 7,067,274 B2
APPLICATION NO. : 10/983495
DATED : June 27, 2006
INVENTOR(S) : Wayne J. Fairbrother et al.

It is certified that error appears in the above-identified patent and that said Letters Patent is hereby corrected as shown below:

In column 11, lines 4, please replace "XAP" with --XIAP--.

In column 14, line 16, please replace "interesl" with -- interest. --.

In column 25, line 53, please replace "PCF" with -- PCT --.

In column 67, line 19, please replace "initailly" with -- initially --.

In column 68, line 40, please replace "ML-AP" with -- ML-IAP --.

In column 68, line 54, please replace "anti-MIAP" with -- anti-ML-IAP --.

In column 72, line 27, please replace "MIAP" with -- ML-IAP --.

In column 81, line 16, please replace "coimnunoprecipitates" with -- co-immunoprecipitates--.

Signed and Sealed this

Eleventh Day of September, 2007

JON W. DUDAS
*Director of the United States Patent and Trademark Office*

```
                          SEQUENCE LISTING

<160> NUMBER OF SEQ ID NOS: 10

<210> SEQ ID NO 1
<211> LENGTH: 399
<212> TYPE: DNA
<213> ORGANISM: Homo sapien

<400> SEQUENCE: 1
atgggcagca gccatcatca tcatcatcac agcagcggcc tggtgccgcg              50
cggcagccat atgctcgaga cagaggagga agaggaggag ggcgccgggg             100
ccaccttgtc caggggggcct gccttccccg gcatgggctc tgaggagttg             150
cgtctggcct ccttctatga ctggccgctg actgctgagg tgccacccga             200
gctgctggct gctgccggct tcttccacac aggccatcag gacaaggtga             250
ggtgcttctt ctgctatggg ggcctgcaga gctggaagcg cggggacgac             300
ccctggacgg agcatgccaa gtggttcccc ggttgtcagt tcctgctccg             350
gtcaaaagga caagaatata taaacaatat tcatttaact cattcactt              399

<210> SEQ ID NO 2
<211> LENGTH: 133
<212> TYPE: PRT
<213> ORGANISM: Homo sapien

<400> SEQUENCE: 2

Met Gly Ser Ser His His His His His His Ser Ser Gly Leu Val
 1               5                  10                  15

Pro Arg Gly Ser His Met Leu Glu Thr Glu Glu Glu Glu Glu Glu
                20                  25                  30
```

-continued

```
Gly Ala Gly Ala Thr Leu Ser Arg Gly Pro Ala Phe Pro Gly Met
             35                  40                  45

Gly Ser Glu Glu Leu Arg Leu Ala Ser Phe Tyr Asp Trp Pro Leu
         50                  55                  60

Thr Ala Glu Val Pro Pro Glu Leu Leu Ala Ala Gly Phe Phe
         65                  70                  75

His Thr Gly His Gln Asp Lys Val Arg Cys Phe Phe Cys Tyr Gly
         80                  85                  90

Gly Leu Gln Ser Trp Lys Arg Gly Asp Asp Pro Trp Thr Glu His
         95                 100                 105

Ala Lys Trp Phe Pro Gly Cys Gln Phe Leu Leu Arg Ser Lys Gly
             110                 115                 120

Gln Glu Tyr Ile Asn Asn Ile His Leu Thr His Ser Leu
             125                 130
```

```
<210> SEQ ID NO 3
<211> LENGTH: 6
<212> TYPE: PRT
<213> ORGANISM: Artificial sequence
<220> FEATURE:
<223> OTHER INFORMATION: Synthetic derived from Drosophila melanogaster

<400> SEQUENCE: 3

Ala Val Pro Phe Ala Lys
 1               5

<210> SEQ ID NO 4
<211> LENGTH: 9
<212> TYPE: PRT
<213> ORGANISM: Artificial sequence
<220> FEATURE:
<223> OTHER INFORMATION: Synthetic derived from Homo Sapien

<400> SEQUENCE: 4

Ala Val Pro Ile Ala Gln Lys Ser Glu
 1               5

<210> SEQ ID NO 5
<211> LENGTH: 4
<212> TYPE: PRT
<213> ORGANISM: Artificial sequence
<220> FEATURE:
<223> OTHER INFORMATION: Synthetic derived from Drosophila Melanogaster

<400> SEQUENCE: 5

Ala Val Pro Trp
 1

<210> SEQ ID NO 6
<211> LENGTH: 16
<212> TYPE: PRT
<213> ORGANISM: Artificial sequence
<220> FEATURE:
<223> OTHER INFORMATION: Synthetic derived from Drosophila melanogaster

<400> SEQUENCE: 6

Arg Gln Ile Lys Ile Trp Phe Gln Asn Arg Arg Met Lys Trp Lys
 1               5                  10                  15
Lys

<210> SEQ ID NO 7
<211> LENGTH: 117
<212> TYPE: PRT
```

<213> ORGANISM: Homo sapien

<400> SEQUENCE: 7

```
Thr Glu Glu Glu Glu Glu Gly Ala Gly Ala Thr Leu Ser Arg
  1               5                  10                  15

Gly Pro Ala Phe Pro Gly Met Gly Ser Glu Glu Leu Arg Leu Ala
                 20                  25                  30

Ser Phe Tyr Asp Trp Pro Leu Thr Ala Glu Val Pro Pro Glu Leu
             35                  40                  45

Leu Ala Ala Ala Gly Phe Phe His Thr Gly His Gln Asp Lys Val
             50                  55                  60

Arg Cys Phe Phe Cys Tyr Gly Gly Leu Gln Ser Trp Lys Arg Gly
             65                  70                  75

Asp Asp Pro Trp Thr Glu His Ala Lys Trp Phe Pro Ser Cys Gln
             80                  85                  90

Phe Leu Leu Arg Ser Lys Gly Arg Asp Phe Val His Ser Val Gln
             95                 100                 105

Glu Thr His Ser Gln Leu Leu Gly Ser Trp Asp Pro
            110                 115
```

<210> SEQ ID NO 8
<211> LENGTH: 110
<212> TYPE: PRT
<213> ORGANISM: Homo sapien

<400> SEQUENCE: 8

```
Thr Glu Glu Glu Glu Glu Gly Ala Gly Ala Thr Leu Ser Arg
  1               5                  10                  15

Gly Pro Ala Phe Pro Gly Met Gly Ser Glu Glu Leu Arg Leu Ala
                 20                  25                  30

Ser Phe Tyr Asp Trp Pro Leu Thr Ala Glu Val Pro Pro Glu Leu
             35                  40                  45

Leu Ala Ala Ala Gly Phe Phe His Thr Gly His Gln Asp Lys Val
             50                  55                  60

Arg Cys Phe Phe Cys Tyr Gly Gly Leu Gln Ser Trp Lys Arg Gly
             65                  70                  75

Asp Asp Pro Trp Thr Glu His Ala Lys Trp Phe Pro Ser Cys Gln
             80                  85                  90

Phe Leu Leu Arg Ser Lys Gly Arg Asp Phe Val His Ser Val Gln
             95                 100                 105

Glu Thr His Ser Gln
            110
```

<210> SEQ ID NO 9
<211> LENGTH: 110
<212> TYPE: PRT
<213> ORGANISM: Homo sapien

<400> SEQUENCE: 9

```
Thr Glu Glu Glu Glu Glu Gly Ala Gly Ala Thr Leu Ser Arg
  1               5                  10                  15

Gly Pro Ala Phe Pro Gly Met Gly Ser Glu Glu Leu Arg Leu Ala
                 20                  25                  30

Ser Phe Tyr Asp Trp Pro Leu Thr Ala Glu Val Pro Pro Glu Leu
             35                  40                  45

Leu Ala Ala Ala Gly Phe Phe His Thr Gly His Gln Asp Lys Val
             50                  55                  60
```

```
                            -continued

Arg Cys Phe Phe Cys Tyr Gly Gly Leu Gln Ser Trp Lys Arg Gly
                65                  70                  75

Asp Asp Pro Trp Thr Glu His Ala Lys Trp Phe Pro Gly Cys Gln
                80                  85                  90

Phe Leu Leu Arg Ser Lys Gly Gln Glu Tyr Ile Asn Asn Ile His
                95                 100                 105

Leu Thr His Ser Leu
                110

<210> SEQ ID NO 10
<211> LENGTH: 108
<212> TYPE: PRT
<213> ORGANISM: Homo sapien

<400> SEQUENCE: 10

Ser Asp Ala Val Ser Ser Asp Arg Asn Phe Pro Asn Ser Thr Asn
  1               5                  10                  15

Leu Pro Arg Asn Pro Ser Met Ala Asp Tyr Glu Ala Arg Ile Phe
                 20                  25                  30

Thr Phe Gly Thr Trp Ile Tyr Ser Val Asn Lys Glu Gln Leu Ala
                 35                  40                  45

Arg Ala Gly Phe Tyr Ala Leu Gly Glu Gly Asp Lys Val Lys Cys
                 50                  55                  60

Phe His Cys Gly Gly Gly Leu Thr Asp Trp Lys Pro Ser Glu Asp
                 65                  70                  75

Pro Trp Glu Gln His Ala Lys Trp Tyr Pro Gly Cys Lys Tyr Leu
                 80                  85                  90

Leu Glu Gln Lys Gly Gln Glu Tyr Ile Asn Asn Ile His Leu Thr
                 95                 100                 105

His Ser Leu
```